United States Patent
De La Fuente Gonzalez et al.

(10) Patent No.: US 10,111,935 B2
(45) Date of Patent: Oct. 30, 2018

(54) AGENT FOR CAPTURING TUMOR CELLS AND METHODS OF USE THEREOF

(71) Applicants: FUNDACIÓN PEDRO BARRIÉ DE LA MAZA, CONDE DE FENOSA, La Coruña (ES); SERGAS, La Coruña (ES); UNIVERSITY OF SANTIAGO DE COMPOSTELA, La Coruña (ES); FUNDACION RAMÓN DOMINGUEZ, La Coruña (ES); BIOMERIX CORPORATION, Somerset, NJ (US)

(72) Inventors: Alexandre De La Fuente Gonzalez, Santiago de Compostela (ES); Rafael Lopez, Santiago de Compostela (ES); Miguel Abal Posada, Santiago de Compostela (ES); Lawrence Patrick Lavelle, Jr., Colonia, NJ (US)

(73) Assignees: FUNDACIÓN PEDRO BARRIÉ DE LA MAZA, CONDO DE FENOSA, La Coruña (ES); SERGAS, La Coruña (ES); UNIVERSITY OF SANTIAGO DE COMPOSTELA, La Coruña (ES); FUNDACION RAMÓN DOMINGUEZ, La Coruña (ES); BIOMERIX CORPORATION, Somerset, NJ (US)

(*) Notice: Subject to any disclaimer, the term of this patent is extended or adjusted under 35 U.S.C. 154(b) by 0 days.

(21) Appl. No.: 15/307,642

(22) PCT Filed: Apr. 30, 2015

(86) PCT No.: PCT/EP2015/059602
§ 371 (c)(1),
(2) Date: Oct. 28, 2016

(87) PCT Pub. No.: WO2015/166089
PCT Pub. Date: Nov. 5, 2015

(65) Prior Publication Data
US 2017/0049860 A1 Feb. 23, 2017
US 2017/0246258 A2 Aug. 31, 2017

(30) Foreign Application Priority Data

Apr. 30, 2014 (EP) .................................. 14382160
Jan. 29, 2015 (GB) .................................. 1501474.9

(51) Int. Cl.
| | |
|---|---|
| A61K 9/00 | (2006.01) |
| B01J 20/26 | (2006.01) |
| B01J 20/30 | (2006.01) |
| B01J 20/32 | (2006.01) |
| A61K 38/39 | (2006.01) |
| A61K 47/34 | (2017.01) |
| A61K 45/06 | (2006.01) |
| A61K 9/19 | (2006.01) |

(52) U.S. Cl.
CPC ............ *A61K 38/39* (2013.01); *A61K 9/0024* (2013.01); *A61K 9/19* (2013.01); *A61K 45/06* (2013.01); *A61K 47/34* (2013.01); *B01J 20/262* (2013.01); *B01J 20/3021* (2013.01); *B01J 20/3212* (2013.01); *B01J 20/3225* (2013.01); *B01J 20/3274* (2013.01)

(58) Field of Classification Search
CPC ...... A61K 9/0019; A61K 9/0024; A61K 9/19; A61K 38/39; A61K 47/34; B01J 20/262; B01J 20/3208; B01J 20/3212; B01J 20/3225; B01J 20/3274; B01J 20/3021; B01J 20/3078
See application file for complete search history.

(56) References Cited

U.S. PATENT DOCUMENTS

| | | | |
|---|---|---|---|
| 4,776,173 | A | 10/1988 | Kamarei |
| 5,153,067 | A | 10/1992 | Eiichi |
| 7,803,395 | B2 | 9/2010 | Datta |
| 8,337,487 | B2 | 12/2012 | Datta |
| 2010/0159008 | A1 | 6/2010 | Barron |

(Continued)

FOREIGN PATENT DOCUMENTS

| | | |
|---|---|---|
| WO | 2003/011330 A1 | 2/2003 |
| WO | 2009002401 | 12/2008 |

(Continued)

OTHER PUBLICATIONS

"Anonymous, ""Q&A: Caught in a trap—UT Arlington Inquiry Magazine (2012),"" Inquiry—The Research Magazine for the Universoty of Texas at Arlington, Sep. 20, 2012, http://www.uta.edu/ucomm/researchmagazine/2012/cancer/caught-in-a-trap.php, (retrieved Oct. 21, 2015)".

Ahmed et al., "Role of integrin receptors for fibronectin, collagen and laminin in the regulation of ovarian carcinoma functions in response to a matrix microenvironment", Clin Exp Metastasis, 22(5):391-402 (2005).

Burleson et al., "Ovarian carcinoma ascites spheroids adhere to extracellular matrix components and mesothelial cell monolayers", Gynecol Oncol, 93(1):170-181 (2004).

(Continued)

*Primary Examiner* — Jeffrey E. Russel
(74) *Attorney, Agent, or Firm* — Nixon Peabody LLP; Mark J. FitzGerald; Srividya Subramanian

(57) ABSTRACT

The present invention relates to a composition for modulating tumor cell dissemination, in particular metastatic cancer cells. In particular, the invention relates to an agent for modulating metastatic tumor cell dissemination for use in the treatment and/or prevention of a metastatic cancer wherein the agent comprises an extracellular matrix (ECM) protein carried on a polycarbonate polyurethane matrix, and wherein the agent binds to tumor cells when implanted in a body. The invention also relates to a product, comprising an agent for modulating metastatic tumor cell dissemination, and to a method of treatment or prevention of cancer.

6 Claims, 24 Drawing Sheets

(56) References Cited

U.S. PATENT DOCUMENTS

Figure 1:
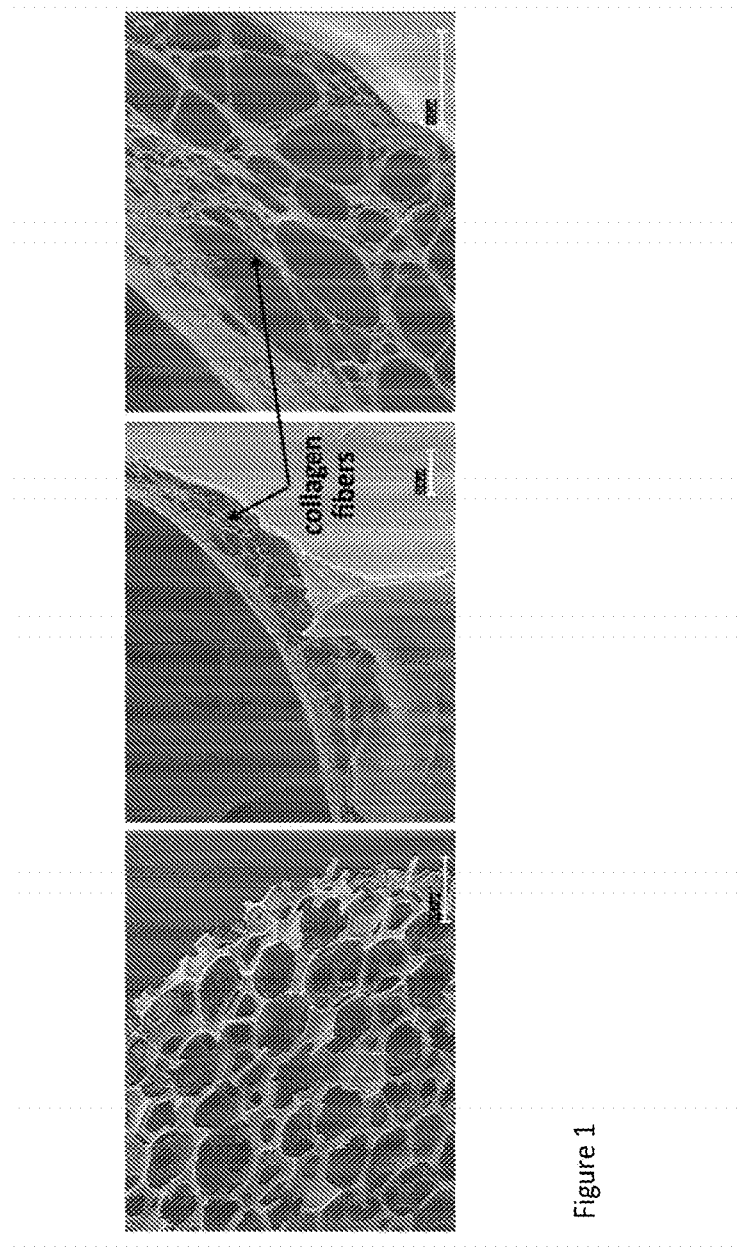

| | | |
|---|---|---|
| 2011/0020216 A1 | 1/2011 | Mooney |
| 2014/0072510 A1 | 3/2014 | Shea |

FOREIGN PATENT DOCUMENTS

| | | |
|---|---|---|
| WO | 2011/090778 A1 | 7/2011 |
| WO | 2012/019049 A1 | 2/2012 |
| WO | 2014063128 | 4/2014 |
| WO | 2014083019 | 6/2014 |

OTHER PUBLICATIONS

Caicedo-Carvajal et al., "Cancer Tissue Engineering: A Novel 3D Polystyrene Scaffold for In Vitro Isolation and Amplification of Lymphoma Cancer Cells from Heterogeneous Cell Mixtures", J Tissue Eng, 2011:362326 (2011) 10 pp.

Cao et al., "Electrospun nanofibers as a bioadhesive platform for capturing adherent leukemia cells", J Biomed Mater Res A, 102(2):523-31 (2014).

Damanik et al., "Towards an in vitro model mimicking the foreign body response: tailoring the surface properties of biomaterials to modulate extracellular matrix", Sci Rep, 4:6325 (2014).

De La Fuente et al., "M-Trap: Exosome-Based Capture of Tumor Cells as a New Technology in Peritoneal Metastasis", J Natl Cancer Inst, 107(9) (2015) 10pp.

De Vlieghere et al., "Tumor-environment biomimetics delay peritoneal metastasis formation by deceiving and redirecting disseminated cancer cells", Biomaterials, 54:148-157 (2015).

Frantz et al., "The extracellular matrix at a glance", J Cell Sci, 123(Pt 24):4195-4200 (2010).

Guo et al., "Controllable metastasis: the trap for the esophageal cancer cells?", Med Hypotheses, 74(6):1000-1001 (2010).

Harrison, Tumors in Primordial Animals Suggest Cancer Can't Be Prevented, Aug. 26, 2014, accessed at www.medscape.com.

Hou et al., "Collagen attachment to the substrate controls cell clustering through migration", Phys Biol, 11(5):056007 (2014) 13 pp.

'International Preliminary Report on Patentability, PCT appl. No. PCT/EP2013/074794, 12 pages(dated Jun. 2, 2015)'.

International Search Report, PCT appl. No. PCT/EP2013/074794, 9 pages (dated Jun. 2, 2014).

Jain et al., "Guiding intracortical brain tumour cells to an extracortical cytotoxic hydrogel using aligned polymeric nanofibres", Nat Mater, 13(3):308-316 (2014).

Karagiannis et al., "Cancer-associated fibroblasts drive the progression of metastasis through both paracrine and mechanical pressure on cancer tissue", Mol Cancer Res, 10(11):1403-1418 (2012).

Ko et al., "The use of chemokine-releasing tissue engineering scaffolds in a model of inflammatory response-mediated melanoma cancer metastasis", Biomaterials, 33(3):876-885 (2012).

Levental et al., "Matrix crosslinking forces tumor progression by enhancing integrin signaling", Cell, 139(5):891-906 (2009).

Liang et al., "Rapid adherence to collagen IV enriches for tumour initiating cells in oral cancer", Eur J Cancer, 50 (18):3262-3270 (2014).

Lu et al., "Isolation of circulating epithelial and tumor progenitor cells with an invasive phenotype from breast cancer patients", Int J Cancer, 126(3):669-683 (2010).

Ma et al., "Trap Effect of Three-Dimensional Fibers Network for High Efficient Cancer-Cell Capture", Adv Healthc Mater, 4(6):838-843 (2015).

Madhavan et al., "Evaluation of composition and crosslinking effects on collagen-based composite constructs", Acta Biomater, 6(4):1413-1422 (2010).

McIntosh, et al., "Control of Mammalian Cell Behaviour Through Mimicry of the Extracellular Matrix Environment", Intech Open Access Publisher (2011) 20 pp.

Mignot et al., "Prospects for exosomes in immunotherapy of cancer", J Cell Mol Med, 10(2):376-388 (2006).

Moreau et al., "Tissue-engineered bone serves as a target for metastasis of human breast cancer in a mouse model", Cancer Res, 67(21):10304-10308 (2007).

Rizwan et al., "Metastatic breast cancer cells in lymph nodes increase nodal collagen density", Sci Rep, 5:10002 (2015).

Seib et al., "Tissue engineering a surrogate niche for metastatic cancer cells", Biomaterials, 51:313-319 (2015).

Silk et al., "Effect of pluronic-F68 on the development of tumor metastasis", Cancer, 29(1):171-172 (1972).

Tang, "Development of cancer traps for prolonging lifespan by eliminating metastatic cancer cells," Cancer Prevention and Research Institute of Texas, Nov. 3, 2011, http://www.cprit.state.tx.us/files/funded-grants/RP120572.pdf, (retrieved Oct. 21, 2015).

Williamson., "Exercise for Special Populations", 2011, Lippincott Williams & Wilkins, 1st Ed., p. 350.

Written Opinion of the International Searching Authority, PCT appl. No. PCT/EP2013/074794, 11 pages (dated Jun. 2, 2014).

Anonymous: "Biomerix 3D Scaffold(TM)", XP055204491; retreived from http://cellon.lu/wa_files/Biomerix_203D_20Scaffold_20Brochure.pdf, Jan. 1, 2010.

AGENT FOR CAPTURING TUMOR CELLS AND METHODS OF USE THEREOF

CROSS-REFERENCE TO RELATED APPLICATIONS

This application is a 35 U.S.C. § 371 National Phase Entry Application of International Application No. PCT/EP2015/059602 filed Apr. 30, 2015, which designated the U.S., and which claims benefit of EP Application No. 14382160.1 filed Apr. 30, 2014, and which claims benefit of GB Application No. 1501474.9 filed Jan. 29, 2015.

The present invention relates to an agent for modulating the dissemination of cancer cells, in particular metastatic cancer cells, and to the use of the agent in the treatment or prevention of cancer. The composition may capture and/or attract cancer cells, in particular metastatic cancer cells. The invention also relates to a method of treatment or prevention of cancer.

The process of metastasis is associated with more than 90% of cancer-related deaths and represents the main challenge in oncology. While primary disease is reasonably accessible to surgery and/or radiotherapy and presents an acceptable response to chemotherapy leading to a good prognosis; metastatic dissemination is associated with a contraindication to surgery and radiotherapy and especially resistance to chemotherapy, and offers a much worse prognosis.

In recent years, the process of metastasis has been characterized as a stepwise process where aggressive tumor cells acquire the abilities to invade the surrounding stroma and tissues, to intravasate and survive in the blood flow, and to extravasate and generate a micrometastasis at distant organs. In general, there are two main ways of tumor cell dissemination from the primary lesion: systemic dissemination of metastatic tumor cells through the blood and lymphatic vessels, and loco-regional dissemination by release or migration/invasion of metastatic tumor cells into the surroundings. Tumor cells which disseminate from the primary tumor into the bloodstream, are known as circulating tumor cells (CTC), and are the main cause of metastasis. For dissemination through blood and lymphatic vessels, the consensus is that tumor cells must acquire an aggressive phenotype allowing migration and invasion of the surrounding stroma (epithelial to mesenchymal transition); activate neoangiogenesis by attracting endothelial cells and creating new blood vessels that provide the tumor not only with nutrients but also generating routes for dissemination; then tumor cells invade and incorporate into the new blood vessels (intravasation) and disseminate to those sites in the organism where they will attach and exit the blood vessels (extravasation); finally, these metastatic tumor cells will be able to establish a niche and generate a micrometastasis that will evolve into a metastatic lesion. The whole process is extremely inefficient but dramatically lethal. Alternatively, dissemination may occur through cellular migration and invasion of the surrounding stroma and organs, or like in ovarian cancer where tumor cells are exposed and released to the peritoneal cavity, by incorporation of metastatic cells into the ascitic fluid and implantation in the peritoneum and organs accessible in the cavity.

The molecular and cellular bases that determine the process of metastasis suggest an intense dialogue of the primary tumor with the environment (Sleeman, J P et al., Semin Cancer Biol. 2012 June; 22(3):174-86). Tissue specific metastasis (Nguyen et al., Nat Rev Cancer. 2009; 9(4):274-84) and pre-metastatic niches (Psaila & Lyden, Nat Rev Cancer. 2009; 9(4):285-93) are concepts that are beginning to illustrate an active role of carcinomas in the determination of the most adequate sites to colonize: signals emitted from the tumor and from the environment may govern the remodeling of targeted tissues for a favored reception of tumor cells disseminated from primary lesions.

An aim of the present invention is to interfere with the communication between tumor cells, and in particular metastatic tumor cells, and the host, to allow the pattern of metastatic dissemination to be modulated. The invention may operate, in certain embodiments, by physically trapping such cells and/or by providing a preferential site for homing of such cells.

According to a first aspect, the invention provides an agent for modulating tumor cell dissemination comprising an extracellular matrix protein (ECM) or adhesion molecule and a reticulated elastomeric matrix for use in the treatment and/or prevention of a cancer.

The invention also provides the use of an agent for modulating tumor cell dissemination comprising an extracellular matrix protein (ECM) or adhesion molecule and a reticulated elastomeric matrix in the treatment and/or prevention of cancer.

The invention also further provides the use of an agent for modulating tumor cell dissemination comprising an extracellular matrix protein (ECM) or adhesion molecule and a reticulated elastomeric matrix in the preparation of a medicament or a medical device for the treatment and/or prevention of cancer. The medical device may have a non-pharmacological mode of action.

Preferably the agent for modulating tumor cell dissemination is for modulating metastatic tumor cell dissemination. Preferably the agent is for use in the treatment and/or prevention of a metastatic cancer.

The agent for modulating tumor cell dissemination may act to interfere with the natural process of tumor cell dissemination, preferably to modulate the behaviour of such cells such that they are attracted to or captured at a particular site, preferably at the location of the agent for modulating tumor cell dissemination.

The agent for modulating tumor cell dissemination may act as a chemoattractant for tumor cells, in particular for metastatic tumor cells. The metastatic tumor cells may be circulating tumor cells, disseminated tumor cells or any cell disseminated from a primary tumor.

The agent for modulating tumor cell dissemination may be intended to capture or trap tumor cells, and in particular metastatic tumor cells, such as circulating tumor cells, disseminated tumor cells or any cell disseminated from a primary tumor. The agent may directly mediate capture of the tumor cells, for example by adhering to the tumor cells, or may have an indirect effect which improves adhesion of the tumor cells at specific sites in the host.

The reticulated elastomeric matrix may be a polycarbonate polyurethane matrix, the polymer of the matrix may be cross linked; the polymer may also contain urea within the molecular structure.

An agent for use in the invention may further be capable of physically capturing tumor cells and trapping them, the agent may be an adhesive material to which tumor cells adhere.

The agent may capture/trap the cells by providing a favoured substrate for the metastatic cells to attach and anchor to. This substrate may be a solid 2D or 3D polymer surface, or a chemically modified surface, or a patterned surface, or a gel, or a hydrogel, etc, where the cell can create adhesive structures such as focal adhesions, tight junctions, anchoring junctions, GAP junctions, etc.

The agent may comprise a 2D or a 3D porous structure. In one embodiment the capture agent may be a 3D porous tissue scaffold type material. The agent may be a 3D porous mesh structure.

The 2D or 3D surface or structure may be provided by the reticulated elastomeric matrix, such as a polycarbonate polyurethane matrix, preferably with one or more ECM proteins contained or carried therein. The polycarbonate polyurethane structure may be cross-linked with urea.

The agent may comprise a polycarbonate polyurethane matrix with urea segments and additional crosslinking, such as the Biomerix™ 3D Scaffolds from Sigma Aldrich, USA.

The one or more ECM proteins may be physically and/or chemically contained or carried in the reticulated elastomeric matrix, such as a polycarbonate polyurethane matrix. The ECM proteins may be permanently contained within the matrix or they may be released in a controlled or uncontrolled manner.

The agent of the invention may comprise a 2D or a 3D scaffold of a reticulated elastomeric matrix, such as a polycarbonate polyurethane matrix, which is decorated with or has embedded therein ECM proteins to improve the attachment of tumor cells, and metastatic tumor cells in particular, to the surface. The ECM proteins may mediate cell-cell adhesion or cell-substrate adhesion. In addition, the agent may capture/trap the metastatic cells by remodeling the site of implantation of the invention, by means of remodeling the cellular architecture of the site of implantation, or by remodeling the extracellular matrix, by remodeling the site through a foreign body reaction (Anderson et al., Semin Immunol 2008) or an inflammatory reaction.

The agent for modulating tumor cell dissemination may alternatively or additionally comprise a chemoattractant for tumor cells, and in particular metastatic tumor cells, such as circulating tumor cells, disseminated tumor cells or any cell disseminated from a primary tumor.

In some embodiments the agent for modulating tumor cell dissemination may therefore act as both a capture agent and a chemoattractant for tumor cells.

Useful chemoattractants may be any agent capable of attracting tumor cells, and in particular metastatic tumor cells, such as circulating tumor cells, disseminated tumor cells or any cell disseminated from a primary tumor. The tumor cells may be attracted directly or indirectly through the attraction of an intermediate cell (i.e. immune cell or stem cell). For example, the implantation of an agent of the invention may generate an inflammatory reaction that provides an additional chemotactic effect for metastatic cancer cells. Furthermore, the tumor cells that are attracted by the agent of the invention may themselves provide an additional chemotactic effect for other tumor cells, and in particular metastatic tumor cells.

The agent for modulating tumor cell dissemination may further comprise vesicles derived from cells, including exosomes. Exosomes are cell-derived microvesicles that are present in many and perhaps all biological fluids, including blood, urine, and ascitic fluid. They typically have a diameter of between 30 and 100 nm. They are released by many cells types during normal physiological processes; however tumors appear to aberrantly secrete large quantities of exosomes. Exosomes for use in the invention may be obtained from a bodily fluid, such as blood or urine, or obtained from many different cell types in an organism. The bodily fluid from which exosomes are purified may be from a healthy donor. Exosomes for use in the invention may be secreted by cancer cells, such as ovarian cancer cells; or alternatively, or in addition, the exosomes may be secreted by non cancer cells, such as mesenchymal stem cells. It may be preferable to use exosomes from non cancer cells Alternatively, or additionally, the agent for modulating tumor cell dissemination may further comprise ascitic fluid from a subject with ovarian cancer. The ascitic fluid may comprise exosomes. The capture agent or chemoattractant may be exosomes obtained from the ascitic fluid of a subject with ovarian cancer.

Alternatively, or additionally, the agent for modulating tumor cell dissemination may further comprise mesenchymal stem cells themselves, or indeed another form of stem cells, but preferably not human embryonic stem cells. Mesenchymal stem cells of adipose, umbilical cord or bone marrow origin may be used as a chemoattractant.

Alternatively or additionally, the agent for modulating tumor cell dissemination may further comprise a cell adhesion molecule, such as a selectin, a member of the immunoglobulin (Ig) superfamily, an integrin or a cadherin. The cell adhesion molecule may be found associated with exosomes such as CD9 and/or CD81.

Alternatively, or additionally, the agent for modulating tumor cell dissemination may further comprise one or more chemokines and/or one or more growth factors, for example one or more of SDF1, 90K, osteopontin, EGF, TGFb1, FGF, and IGF. In one embodiment the chemoattractant comprises a combination of EGF, TGFb1 and FGF.

The agent for modulating tumor cell dissemination preferably includes one or more adhesion molecule or extracellular matrix component selected from the list comprising cell adhesion molecules, calcium-independent IgSF, CAM, N-CAM (Myelin protein zero), ICAM (1, 5), VCAM-1, PE-CAM, L1-CAM, Nectin (PVRL1, PVRL2, PVRL3), integrins, LFA-1 (CD11a+CD18), integrin alphaXbeta2 (CD11c+CD18), macrophage-1 antigen (CD11b+CD18), VLA-4 (CD49d+CD29), glycoprotein IIb/IIIa (ITGA2B+ITGB3), Calcium-dependent cadherins, Classical CDH1, CDH2, CDH3, desmosomal Desmoglein (DSG1, DSG2, DSG3, DSG4), desmocollin (DSC1, DSC2, DSC3), protocadherin, PCDH1, PCDH15, unconventional/ungrouped T-cadherin, CDH4, CDH5, CDH6, CDH8, CDH11, CDH12, CDH15, CDH16, CDH17, CDH9, CDH10, selectins, E-selectin, L-selectin, P-selectin, other lymphocyte homing receptors, CD44, L-selectin, integrin (VLA-4, LFA-1), carcinoembryonic antigen, CD22, CD24, CD44, CD146, CD164, proteins and glycosaminoglycans as components of the extracellular matrix (ECM): heparan sulfate, chondroitin sulfates, keratan sulfates, hyaluronic acid, collagens, elastins, fibrillin, fibronectins and laminins.

The agent may comprise a component of the extracellular matrix (ECM), including one or more of heparan sulfate, chondroitin sulfates, keratan sulfates, hyaluronic acid, collagens, elastins, fibrillin, fibronectins and laminins. The agent may comprise collagen and/or fibronectin.

If included, a further chemoattractant may remain attached to or within the matrix of the agent of the invention, or may be released or leached from the matrix to create a gradient of chemoattractant around the matrix.

The agent is biocompatible, such that if placed in a human or non-human animal it does not cause an unacceptable immune response. In some embodiments the agent may be associated with a limited immune response at the site of placement, for example an inflammatory immune response or foreign body reaction.

The agent may comprise a porous matrix as described above. The matrix may be a 2D or a 3D porous structure. In one embodiment the matrix may be a 3D porous tissue scaffold type material. The matrix may be a 3D porous mesh structure.

Where the agent includes a chemoattractant, which may or may not be the one or more ECM proteins, the agent may create a gradient of the chemoattractant, essentially by releasing the chemoattractant over time. The chemoattractant may be released in a controlled or an uncontrolled manner. Release of the chemoattractant may be active or passive, or both. The chemoattractant may be the one or more ECM proteins.

Preferably the agent, in use, retains at least 10%, 20% 30%, 40%, 50% or more of the chemoattractant and or ECM proteins for at least 12 hours, at least 24 hours, at least 48 hours, at least 3 days, at least 4 days, at least 5 days, at least 6 days, at least 1 week, at least 2 weeks, at least 3 weeks, at least 4 weeks or longer. Preferably the agent is quite stable and no significant ECM protein is released, preferably over 80% of the ECM protein is retained in or on the matrix for at least a week when in use. In another embodiment, over 80% of the ECM protein is retained in or on the matrix for at least a month when in use. In another embodiment, over 80% of the ECM protein is retained in or on the matrix for at least 3 months or 6 months when in use. In another embodiment, over 80% of the ECM protein is retained in or on the matrix for at least 12 months when in use.

The agent, in use, may release at least 10%, 20% 30%, 40%, 50% or more of the chemoattractant and or ECM proteins over at least 12 hours, at least 24 hours, at least 48 hours, at least 3 days, at least 4 days, at least 5 days, at least 6 days, at least 1 week, at least 2 weeks, at least 3 weeks, at least 4 weeks or longer.

The agent, in use, may create a chemoattractant gradient for at least 12 hours, at least 24 hours, at least 48 hours, at least 3 days, at least 4 days, at least 5 days, at least 6 days, at least 1 week, at least 2 weeks, at least 3 weeks, at least 4 weeks or longer.

Preferably the agent of the invention is able to release sufficient chemoattractant for modulating tumor cell dissemination to generate a gradient of chemoattractant effective for loco-regional dissemination and/or for systemic dissemination in a subject for a period sufficient to avoid metastatic dissemination.

The agent of the invention may contain, for example, from about 10% to about 98% by weight, preferably about 80%, preferably at least about 20%, 25%, 30%, 35%, 40%, 45%, 50% or more by weight of the ECM protein.

The agent of the invention may contain between 0.1 nanograms and 10 mg of an agent for modulating tumor cell dissemination, such as a capture agent and/or chemoattractant. Preferably between 0.1 nanograms and 1 mg, or 0.1 nanograms and 100 micrograms of the agent for modulating tumor cell dissemination, such as a capture agent and/or chemoattractant. Where the capture agent is collagen the collagen may be present at between about 0.1 μg to 1 mg, e.g. between about 25 μg and 500 μg, e.g. 250 μg.

The agent of the invention may further comprise a chemotherapeutic agent, such as a cytostatic agent. Wherein a cytostatic agent is a pharmacologically active compound capable of inhibiting or suppressing cellular growth and multiplication. Depending on the mechanism of action and on the dose of the compound, it may also represent a cytotoxic agent. In particular, the cytostatic agent may be a compound that is capable of killing, or inhibiting the growth of, tumor cells, preferably metastatic tumor cells, such as circulating tumor cells, disseminated tumor cells or any cell disseminated from a primary tumor.

The cytostatic agent may be selected, for example, from:
a. anthracyclines and analogs thereof, such as daunomycin, doxorubicin, idarubicin, epirubicin, valrubicin, aclacinomycin, and mitoxantrone;
b. antimetabolites, such as gemcitabine, cytosine arabinoside, cytarabine, vidarabine, thioguanine, pentostatin, cladribine, methotrexate, floxuridine, fluorouracil and other fluorinated pyrimidines, purines, or nucleosides;
c. alkylating agents, such as nitrogen mustards, including cyclophosphamide, melphalan, chlorambucil, ifosfamide; nitrosoureas, including carmustine, lomustine, and streptozocin; alkyl sulfonates, including busulfan; thiotepa; platinum compounds, including cisplatin, carboplatin, oxaliplatin, nedaplatin, satraplatin, and triplatin tetranitrate; procarbazine; and altretamine;
d. plant alkaloids and terpenoids, such as vinca alkaloids, including vincristine, vinblastine, vinorelbine, and vindesine; taxanes, including taxol, paclitaxel, docetaxel; and podophyllotoxin;
e. topoisomerase inhibitors, such as amsacrine, etoposide, etoposide phosphate, teniposide and other derivatives of epipodophyllotoxins; irinotecan, topotecan and other camptothecins; and
f. other antineoplastics, such as dactinomycin, bleomycin, mitomycin, etoposide, bleomycin, and plicamycin.

The agent for modulating tumor cell dissemination may be used alone or in combination with other active agents, for example in combination with one or more cytostatic agents.

The agent for modulating tumor cell dissemination of the invention may be placed at a site of use by surgery. Similarly, after use the agent may be removed by surgery.

The agent for modulating tumor cell dissemination of the invention may be intended for use with many types of cancer, including, but not limited to, breast cancer, colorectal cancer, pancreatic cancer, kidney cancer, prostate cancer, urothelial cancer, oesophageal cancer, head and neck cancer, hepatocellular cancer, mesothelioma, Kaposi's sarcoma, ovarian cancer, soft tissue sarcoma, glioma, melanoma, small-cell and non-small-cell lung cancer, endometrial cancer, basal cell carcinoma, transitional cell carcinoma of the urothelial tract, cervical cancer, endometrial cancer, gastric cancer, bladder cancer, uterine sarcoma, multiple myeloma, soft tissue and bone sarcoma, cholangiocarcinoma and cancers disseminated therefrom.

In particular, the agent for modulating tumor cell dissemination of the invention may be intended for use with cancers of the peritoneal cavity, such as, stomach, gall bladder, liver, small intestine, GIST, esophagus, abdominal sarcoma, soft tissue sarcoma, mesothelioma, ovarian, pancreatic, colon, rectal, uterine, cervical, kidney cancer and cancers disseminated therefrom. In a preferred embodiment the cancer is ovarian cancer or a cancer disseminating therefrom. Where the cancer is ovarian cancer or a cancer disseminating therefrom, the product of the invention may be implanted in the abdominal wall of the subject. Alternatively the cancer may be colon cancer. The cancer may be pancreatic cancer.

The present invention may be intended for use in the prevention of cancer metastases, in particular for the prevention of peritoneal metastases.

The agent of the invention may provide a favoured and preferred site for the attachment or implantation of metastatic tumor cells, for example in the peritoneal cavity if that is where the agent is placed. In an embodiment, the agent has a non-pharmacological mode of action when placed in the peritoneal cavity that is further facilitated by the trascoelomic flow present in the peritoneal cavity: that is, cells turn around in the peritoneal cavity and are gradually trapped within the agent of the invention where the agent is acting as a medical device. The agent of the invention may therefore not need to act as a chemoattractant itself, and may simply act to trap metastatic tumor cells.

According to another aspect, the invention provides the use of an agent of the invention that traps or captures metastatic cancer cells in the preparation of a medicament for the treatment or prevention of cancer.

According to another aspect, the invention provides a medical device comprising an agent of the invention that traps or captures metastatic cancer cells. The device may be used for the treatment or prevention of cancer.

Preferably the treatment or prevention of cancer comprises the attraction and/or trapping of tumor cells, and in particular metastatic tumor cells, such as circulating tumor cells, disseminated tumor cells or any cell disseminated from a primary tumor.

Preferably the attracted cells are held or trapped by the action of the agent for modulating tumor cell dissemination, and any chemoattractant present, thus localizing them to a particular location and allowing them to be treated.

The agent for modulating tumor cell dissemination preferably comprises an ECM protein contained in, or attached to, a matrix as described herein. In some embodiments the matrix itself may be an agent for modulating tumor cell dissemination capable of attracting and/or trapping tumor cells, and the provision of a further capture agent and/or chemoattractant is optional. In some embodiments the agent for modulating tumor cell dissemination comprises a 3D polymer scaffold, or hydrogel. Such polymers have been found to have adhesive properties and to be capable of trapping tumor cells, e.g. by providing a niche to which such cells can adhere, and/or by providing a preferential site for homing of such cells.

In some embodiments, the agent for modulating tumor cell dissemination comprises a cross-linked, polycarbonate polyurethane-urea matrix (3D-Kube Biomerix scaffold) decorated with an ECM protein, such as collagen and/or fibronectin.

Preferably the agent for modulating tumor cell dissemination is administered to a non-vital organ. Thus the tumor cells will be attracted to and retained in this tissue and may then be removed by surgery. Such a location may allow any chemoattractant present to be accessible from everywhere in the body; for example, it would allow the agent of the invention to become vascularized and to reach the blood circulation.

Alternatively the agent for modulating tumor cell dissemination may be administered into the fat of a subject.

In a yet further embodiment the agent for modulating tumor cell dissemination may be administered into the peritoneum of a subject to attract and/or capture metastatic cells disseminating in the peritoneal cavity. Similarly, the pleura may be a good place to locate the agent for modulating tumor cell dissemination when treating lung carcinomas and mesotheliomas or tumor cells disseminating into the pleura.

The agent for modulating tumor cell dissemination may be administered by direct injection into the fat of a human or non-human animal. For example, for the attraction of peritoneal metastatic tumor cells the agent for modulating tumor cell dissemination may be injected into the peritoneum or surrounding tissue including fat tissue, for example, the gonadal fat. Alternatively, the agent of the invention may be administered by surgery.

Preferably, once in situ, the agent for modulating tumor cell dissemination causes tumor cells, and in particular metastatic tumor cells, such as circulating tumor cells, disseminated tumor cells or any cell disseminated from a primary tumor, to be attracted to it, and to congregate or be "trapped". In a preferred embodiment the attracted cells are held or trapped by the action of the agent for modulating tumor cell dissemination until the cells are treated. Preferably at least 5%, 10%, 20%. 30%, 40%, 50%, 60%, 70%, 75%, 80%, 85%, 90%, 95%, 98%, 99% or more of the attracted cells are captured by the product of the invention.

The attracted or trapped cells may then be treated. The attracted or trapped cells may be treated by physically removing them, for example by surgery, or by treating them to destroy or inactivate the cells, for example by chemotherapy or radiotherapy. If the agent includes a cytostatic or cytotoxic agent, or the agent for modulating tumor cell dissemination is administered with a cytostatic or cytotoxic agent, then this may act to eradicate or prevent the replication of the attracted cells.

The tumor cells to be treated may be one or more of any of the cancers described above, in particular, the tumor cells may be derived from/disseminated from a peritoneal cancer, such as ovarian cancer.

Preferably the agent of the invention provides an adhesive surface for metastatic cells, and this provides a preferred site of implantation in competition with the natural sites for implantation. The agent may act as an artificial pre-metastatic niche.

According to another aspect the invention provides a method of attracting tumor cells, and in particular metastatic tumor cells, such as circulating tumor cells, disseminated tumor cells or any cell disseminated from a primary tumor, in a subject comprising administering to the subject an agent for modulating tumor cell dissemination, and in particular metastatic tumor cells, such as circulating tumor cells, disseminated tumor cells or any cell disseminated from a primary tumor. The agent for modulating tumor cell dissemination may comprise an ECM protein contained within or attached to a matrix as described with reference to any aspect of the invention. Preferably the attracted cells are retained or trapped by the action of the agent for modulating tumor cell dissemination. Once trapped by the agent for modulating tumor cell dissemination the cancer cells themselves may act as a capture agent and/or chemoattractant for other cancer cells.

According to a still further aspect, the invention provides a method of treating or preventing cancer, in particular a metastatic cancer, comprising administering to a subject in need thereof, an agent for modulating tumor cell dissemination, and in particular metastatic tumor cell dissemination, such as circulating tumor cells, disseminated tumor cells or any cell disseminated from a primary tumor. The agent for modulating tumor cell dissemination may comprise an ECM protein contained within or attached to a matrix as described herein. Preferably the subject in need of treatment has already been diagnosed with a primary cancer, both metastatic or not metastatic. Preferably tumor cells are retained or trapped by the action of the agent for modulating tumor cell dissemination. Preferably the method further comprises the step of treating the trapped cells.

The agent may comprise a polycarbonate polyurethane scaffold with urea segments and additional crosslinking.

The attracted or trapped cells may be treated by physically removing them, for example by surgery, or by treating them to destroy or inactivate the cells, for example by chemotherapy or radiotherapy. If the agent includes a cytostatic or cytotoxic agent then this may act to eradicate or prevent the replication of the attracted cells. The method may comprise the step of surgically removing the attracted cells, and/or the step of administering chemotherapy and/or radiotherapy to treat the attracted or trapped cells.

The method of the present invention may be used in combination with current clinical scenarios, including in combination with one or more of surgery, radiotherapy and chemotherapy.

The cancer may be any cancer, in particular a peritoneal cancer, such as ovarian cancer.

According to a still further aspect the invention provides a medical device or implantable device for use in preventing or treating cancer, preferably metastatic cancer, in a subject, wherein the device comprises an agent for modulating tumor cell dissemination as described herein.

According to another aspect of the invention, there is provided a method of manufacturing an agent for modulating metastatic tumor cell dissemination, the method comprising the steps of:
  preparing a suspended solution of an ECM protein;
  coating the polycarbonate polyurethane matrix by saturation within the solution of the ECM protein; and
  lyophilization of the ECM protein within the polycarbonate polyurethane matrix to form the agent for modulating metastatic tumor cell dissemination.

The skilled man will appreciate that preferred features of any one embodiment and/or aspect and/or claim of the invention may be applied to all other embodiments and/or aspects and/or claims of the invention.

DETAILED DESCRIPTION

Polycarbonate Polyurethane Scaffold

An agent of the invention may comprise a reticulated elastomeric matrix which comprises a network of cells which forms a three-dimensional spatial structure. The cells communicate and connect to each other via the open-celled pores contained within the cells or within the walls of the cells. This network results in a matrix with a unique morphology, composed of continuous interconnected and inter-communicating cells and pores creating a continuous void. The reticulated elastomeric matrix permits in-growth and proliferation of cells and tissue into the implant. Preferably, the reticulated elastomeric matrix is biodurable, is resiliently compressible and preferably comprises polycarbonate polyurethane or polycarbonate polyurethane urea. Suitable matrices include, without limitation, those described in U.S. Pat. Nos. 7,803,395 and 8,337,487; the disclosures of which are hereby incorporated by reference.

Certain embodiments of the invention comprise reticulated biodurable elastomer products, which are also compressible and exhibit resilience in their recovery, that have a diversity of applications and can be employed, by way of example, in biological implantation, especially into humans, for long-term implants that can stay permanently in the body or can be removed from the body after a certain period of time. It would be desirable to form implantable devices suitable for use as scaffolds, tissue engineering scaffolds, cellular growth scaffolds or other comparable substrates, to support in-vivo cell capture, growth, or propagation.

In another embodiment, the implantable devices suitable for use as scaffolds, tissue engineering scaffolds, cellular growth scaffolds or other comparable substrates, to support in-vivo cell capture and propagation. In one embodiment, the reticulated elastomeric matrix of the invention facilitates cell capture and propagation by providing a surface for cellular attachment, migration, proliferation and/or deposition of new tissues, extra-cellular matrix, epithelial tissue connective tissue, areolar tissue, dense regular and irregular tissue, reticular tissue, adipose tissue, cartilage and bone tissue, skeletal, smooth and cardiac muscle tissue, fibrovascular tissue, or any combination thereof. Without being bound by any particular theory, the reticulated implantable devices having a high void content and an unfettered access to the inter-connected and inter-communicating high void content is thought to allow the implantable device to become at least partially ingrown and/or proliferated, in some cases substantially ingrown and proliferated, in some cases completely ingrown and proliferated, with cells and create a preferential site for the capture of disseminated or circulating tumor cells. In another embodiment, owing to the biointegrative three dimensional inter-connected and inter-communicating structure characteristics of the reticulated matrix of the implantable devices of the invention, the agent of the invention has the advantage of potentially better and faster dissemination or circulating tumor cells as compared to natural sites of metastasis.

In another embodiment, reticulated biodurable elastomer products can be satisfactorily implanted or otherwise exposed to living tissue and fluids for extended periods of time, for example, at least 29 days. In one embodiment, the implantable device is biodurable for at least 2 months. In another embodiment, the implantable device is biodurable for at least 6 months. In another embodiment, the implantable device is biodurable for at least 12 months. In another embodiment, the implantable device is biodurable for at least 24 months. In another embodiment, the implantable device is biodurable for at least 5 years. In another embodiment, the implantable device is biodurable for longer than 5 years.

The reticulated biodurable elastomeric products used in the agent of the invention may be described as having a "macrostructure" and a "microstructure", which terms are used herein in the general senses described in the following paragraphs.

The "macrostructure" refers to the overall physical characteristics of an article or object formed of the biodurable elastomeric product of the invention, such as: the outer periphery as described by the geometric limits of the article or object, ignoring the pores or voids; the "macrostructural surface area" which references the outermost surface areas as though any pores thereon were filled, ignoring the surface areas within the pores; the "macrostructural volume" or simply the "volume" occupied by the article or object which is the volume bounded by the macrostructural, or simply "macro", surface area; and the "bulk density" which is the weight per unit volume of the article or object itself as distinct from the density of the structural material.

The "microstructure" refers to the features of the interior structure of the biodurable elastomeric material from which the inventive products are constituted such as cell and pore dimensions; pore surface area, being the total area of the material surfaces in the pores; and the configuration of the struts and intersections that constitute the solid structure of certain embodiments of the inventive elastomeric product. Described generally, the microstructure of the porous biodurable elastomeric matrix having a distinct shape or an extended, continuous entity, comprises a solid phase formed of a suitable biodurable elastomeric material and interspersed there within, or defined thereby, a continuous interconnected void phase, the latter being a principle feature of a reticulated structure and comprises of cells and pores.

The individual cells forming the reticulated elastomeric matrix are characterized by their average cell diameter or, for non-spherical cells, by their largest transverse dimension. The reticulated elastomeric matrix comprises a network of cells that form a three-dimensional spatial structure or void phase which is interconnected via the open pores therein. In one embodiment, the cells form a 3-dimensional superstructure. The pores provide connectivity between the individual cells, or between clusters or groups of pores which form a cell. The cells of the elastomeric matrix are formed from clusters or groups of pores, which would form the walls of a cell except that the cell walls of most of the pores are absent or substantially absent owing to reticulation. In particular, a small number of pores may have a cell wall of structural material also called a "window" or "window pane" such as cell wall. Such cell walls are undesirable to the extent that they obstruct the passage of fluid and/or propagation and proliferation of tissues through pores. Such cell walls that obstruct the passage of fluid and/or propagation and proliferation of tissues through pores may, in one embodiment, be removed in a suitable process step, such as reticulation that can be thermal, explosive or chemical reticulation.

In one embodiment the microstructure of elastomeric matrix is constructed to permit or encourage cellular adhesion to the surfaces of matrix and cellular proliferation into pores of void phase, when elastomeric matrix resides in suitable in-vivo locations for a period of time. In another embodiment, such cellular ingrowth and proliferation can occur or be encouraged not just into exterior layers of pores, but into the deepest interior of and throughout elastomeric matrix. This is possible owing to the presence of interconnected and inter-communicating cells and pores and voids, all of which are accessible for cellular ingrowth and proliferation. Thus, in this embodiment, the space occupied by elastomeric matrix becomes entirely filled by the cellular ingrowth and proliferation except for the space occupied by the elastomeric solid phase.

The void phase may comprise as little as 5% by volume of elastomeric matrix referring to the volume provided by the interstitial spaces of elastomeric matrix. In another embodiment, void phase may comprise as little as 25% by volume of elastomeric matrix. In another embodiment, void phase may comprise as little as 50% by volume of elastomeric matrix. In another embodiment, void phase may comprise as little as 75% by volume of elastomeric matrix. In another embodiment, void phase may comprise as least 90% by volume of elastomeric matrix. In another embodiment, void phase may comprise at least 95% by volume of elastomeric matrix.

In another embodiment the average diameter or other largest transverse dimension of pores is not greater than about 800 µm. In another embodiment the average diameter or other largest transverse dimension of pores is not greater than about 600 µm. In another embodiment, the average diameter or other largest transverse dimension of pores is not greater than about 500 µm. In another embodiment, the average diameter or other largest transverse dimension of pores is not greater than about 400 µm. In another embodiment, the average diameter or other largest transverse dimension of pores is not greater than about 385 µm. In another embodiment, the average diameter or other largest transverse dimension of pores is not greater than about 200 µm. In another embodiment, the average diameter or other largest transverse dimension of pores is not greater than about 100 µm. In another embodiment, the average diameter or other largest transverse dimension of pores is not greater than about 20 µm.

In one embodiment to encourage cellular ingrowth and proliferation and to provide adequate fluid permeability, the average diameter or other largest transverse dimension of the cells of elastomeric matrix is at least about 50 µm. In another embodiment, the average diameter or other largest transverse dimension of it cells is at least about 200 µm. In another embodiment, the average diameter or other largest transverse dimension of it cells is at least about 350 µm. In another embodiment, the average diameter or other largest transverse dimension of it cells is at least about 500 µm. In another embodiment, the average diameter or other largest transverse dimension of it cells is at least about 700 µm. In another embodiment, the average diameter or other largest transverse dimension of it cells is at least about 900 µm. In another embodiment, the average diameter or other largest transverse dimension of it cells is at least about 1500 µm. In another embodiment, the average diameter or other largest transverse dimension of it cells is at least about 1800 µm.

In one embodiment, the elastomeric matrix may have a permeability of greater than 250 Darcy. Alternatively, the elastomeric matrix may have a permeability of greater than 200 Darcy. The elastomeric matrix may have a permeability of less than 500 Darcy. Alternatively, the elastomeric matrix may have a permeability of less than 400 Darcy. Alternatively, the elastomeric matrix may have a permeability of less than 300 Darcy. In one embodiment, the elastomeric matrix may have a permeability of between about 200 Darcy and about 500 Darcy.

In one embodiment, the elastomeric matrix may have a density of between about 3.5 and about 3.9 lb/ft$^3$. In another embodiment, the elastomeric matrix may have a density of between about 2 and about 10 lb/ft$^3$.

The structure, morphology and properties of the elastomeric matrices of this invention can be engineered or tailored over a wide range of performance by varying the starting materials and/or the processing and/or the post processing conditions for different functional or therapeutic uses. In another embodiment, the structure, morphology and properties of the device comprising elastomeric matrices and at least one functional element such as a coating can be engineered or tailored over a wide range of performance by varying the starting materials and/or the processing and/or the post processing conditions.

In one embodiment, the inventive reticulated biodurable elastomeric matrix is synthetic polymers, especially, elastomeric polymers that are resistant to biological degradation, for example, polycarbonate polyurethane-urea, polycarbonate polyurea-urethane, polycarbonate polyurethane. Such elastomers are generally hydrophobic but, pursuant to the invention, may be treated to have surfaces that are less hydrophobic or somewhat hydrophilic. In another embodiment, such elastomers may be produced with surfaces that are less hydrophobic or somewhat hydrophilic. In another embodiment, such elastomers may be produced with surfaces that are significantly or largely hydrophobic.

In further embodiments, the invention provides a porous biodurable elastomer and a process for polymerizing, crosslinking and foaming the same which can be used to produce a biodurable reticulated elastomeric matrix as described herein. In another embodiment, reticulation follows.

More particularly, in another embodiment, the invention provides a biodurable elastomeric polyurethane matrix which comprises synthesizing the matrix from a polycarbonate polyol component and an aromatic diisocyanates such as p-phenylene diisocyanate, 4,4'-diphenylmethane diisocyanate ("4,4'-MDI"), 2,4'-diphenylmethane diisocyanate ("2,4'-MDI") or mixture thereof. The biodurable elastomeric polyurethane matrix is made by polymerization, cross-linking and foaming, thereby forming pores, followed by reticulation of the foam to provide a reticulated product. Reticulation generally refers to a process for at least partially removing cell walls, not merely rupturing or tearing them by a crushing process. Moreover, crushing creates undesirable debris that must be removed by further processing. In another embodiment, the reticulation process substantially fully removes at least a portion of the cell walls. Reticulation may be effected, for example, by at least partially dissolving away cell walls, known variously as "solvent reticulation" or "chemical reticulation": or by at least partially melting, burning and/or exploding out cell walls, known variously as "combustion reticulation". "thermal reticulation" or "explosive reticulation". The product is designated as a polycarbonate polyurethane or polycarbonate polyurethane-urea, being a polymer comprising urethane groups formed from, e.g., the hydroxyl groups of the polycarbonate polyol component and the isocyanate groups of the isocyanate component. In this embodiment, the process employs controlled chemistry to provide a reticulated elastomer product with good biodurability characteristics. Pursuant to the invention, the polymerization is conducted to provide a foam product employing chemistry that avoids biologically undesirable or nocuous constituents therein.

In one embodiment, the invention provides a process for preparing a flexible polyurethane biodurable matrix capable of being reticulated based on polycarbonate polyol component and isocyanate component starting materials. In another embodiment, the foam is substantially free of isocyanurate linkages. In another embodiment, the foam has no isocyanurate linkages. In another embodiment, the foam is substantially free of biuret linkages. In another embodiment, the foam has no biuret linkages. In another embodiment, the foam is substantially free of allophanate linkages. In another embodiment, the foam has no allophanate linkages. In another embodiment, the foam is substantially free of isocyanurate and biuret linkages. In another embodiment, the foam has no isocyanurate and biuret linkages. In another embodiment, the foam is substantially free of isocyanurate and allophanate linkages. In another embodiment, the foam has no isocyanurate and allophanate linkages. In another embodiment, the foam is substantially free of allophanate and biuret linkages. In another embodiment, the foam has no allophanate and biuret linkages. In another embodiment, the foam is substantially free of allophanate, biuret and isocyanurate linkages. In another embodiment, the foam has no allophanate, biuret and isocyanurate linkages.

Collagen Coating of an Elastomeric Matrix

In one embodiment, an elastomeric matrix may have what are referred to herein as "endopore" features as part of its microstructure, i.e., features of elastomeric matrix that are located "within the pores". In one embodiment, the internal surfaces of pores may be "endoporously coated", i.e., coated or treated to impart to those surfaces a degree of a desired characteristic, e.g., hydrophilicity or cell attachment. In one embodiment, the internal surfaces of struts may be "endoporously coated", i.e., coated or treated to impart to those surfaces a degree of a desired characteristic, e.g., hydrophilicity or cell attachment. In one embodiment, the internal void space or the space between the cells may be "endoporously coated", i.e., coated or treated to impart to those surfaces a degree of a desired characteristic, e.g., hydrophilicity or cell attachment. The coating or treating medium can have additional capacity to transport or bond to active ingredients or cells that can then be preferentially delivered to pores. In one embodiment, this coating medium or treatment can be used facilitate attachment, growth and proliferation of cells to the interior pore surfaces. In one embodiment, this coating medium or treatment can be used facilitate growth and proliferation of cells to the interior pore surfaces. In one embodiment, this coating medium or treatment can be used facilitate covalent bonding of materials to the interior pore surfaces. In another embodiment, the coating comprises a biodegradable polymer, a natural polymer, a cellular ingrowth promoter or an inorganic component.

Furthermore, one or more coatings may be applied endoporously by contacting with a biocompatible synthetic polymer, biocompatible synthetic resorbable polymer, natural polymer or cellular ingrowth promoter either in a liquid coating media or in a melt state under conditions suitable to allow the formation of a biocompatible coating, a biocompatible film coating or a biocompatible lyophilized coating. The liquid coating media can be a solution or a slurry or a mixture thereof. In one embodiment, the polymers or the cellular ingrowth promoter used for such coatings are film-forming biocompatible polymers or materials that preferably should adhere to the solid phase. In another embodiment, the polymers or the cellular ingrowth promoter used for such coatings are lyophilizable biocompatible polymers that preferably should adhere to the solid phase. In another embodiment, the bonding strength is such that the film coating or the lyophilized coating does not crack or dislodge during handling or deployment or during placement in the body of reticulated elastomeric matrix.

In one embodiment, the coating is not continuous across the entire external surface of the elastomeric matrix. In another, the coating is not continuous across the entire external surface of the elastomeric matrix such that the permeability and thus the cellular infiltration into the interior surfaces of the elastomeric matrix is not affected. In another, the coating is not continuous across the entire external surface of the elastomeric matrix such that the permeability is moderately affected but still permits cellular infiltration into the elastomeric matrix. It is further thought that as the coating degrades, permeability is restored in cases where they may have been affected, and that circulating cells can invade and infiltrate the reticulated elastomeric matrix in an unfettered fashion.

Suitable biocompatible polymers include bioresorbable aliphatic polyesters include but not limited to polymers and copolymers of lactide (which includes lactic acid d-, l- and meso lactide), ε-caprolactone, glycolide (including glycolic acid), hydroxybutyrate, hydroxyvalerate, para-dioxanone, trimethylene carbonate (and its alkyl derivatives) or a mixture thereof. Suitable biocompatible polymers include hydrophilic polymers and include but not limited to polyethylene glycol, polyvinyl alcohol, polyvinyl acetate or mixture thereof.

In a further embodiment of the invention, described in more detail below, some or all of the pores or the void phase of elastomeric matrix are coated or at least partially filled with a cellular ingrowth promoter. In another embodiment, the promoter can be foamed. In another embodiment, the promoter can be lyophilized. In another embodiment, the promoter can be present as a film. The promoter can be a biodegradable material to promote cellular invasion of elastomeric matrix in-vivo. Promoters include naturally occurring materials that can be enzymatically degraded in the human body or are hydrolytically unstable in the human body, such as collagen, fibrin, fibrinogen, elastin, hyaluronic acid and absorbable biocompatible polysaccharides, such as chitosan, starch, fatty acids (and esters thereof), glucosoglycans and hyaluronic acid. In some embodiments, the pore surface of elastomeric matrix is coated or impregnated, as described in the previous section but substituting the promoter for the biocompatible polymer or adding the promoter to the biocompatible polymer, to encourage cellular ingrowth and proliferation. In a preferred embodiment, the coating is comprised of collagen.

Prior to coating, the collagen may be infiltrated into the void phase of the elastomeric matrix or into the pores of an elastomeric matrix in form of an aqueous collagen slurry, an aqueous collagen suspension or an aqueous collagen solution or a mixture thereof. The collagen may be Type I, II or III or a mixture thereof. In one embodiment, the collagen type comprises at least 70% collagen I. In one embodiment, the collagen type comprises at least 80% collagen I. In one embodiment, the collagen type comprises at least 90% collagen I. The collagen can be derived from a variety human or animal sources, including porcine, bovine, equine, and other animal sources suitable for human use, or may be from a recombinant source. In one embodiment, the collagen can be derived from bovine tendon which is free of bovine spongiform encephalopathy. In one embodiment the collagen comprises or consists of fibrillar Type I bovine collagen. The collagen may be partially denatured, substantially denatured moderately denatured, or slightly denatured. In another embodiment, the collagen can be not denatured.

The concentration of collagen in the collagen slurry, collagen suspension or an aqueous collagen solution may range from about 0.05% to about 4.0% by weight. In another embodiment, the concentration of collagen in the collagen slurry, collagen suspension or an aqueous collagen solution range from about 0.1% to about 2.0% by weight. In another embodiment, the concentration of collagen in the collagen slurry, collagen suspension or an aqueous collagen solution range from about 0.2% to about 1.0% by weight. Alternatively, the concentration of collagen in the collagen slurry, collagen suspension or an aqueous collagen solution may range from about 1% to about 10% by weight. In another embodiment, the concentration of collagen in the collagen slurry, collagen suspension or an aqueous collagen solution range from about 3% to about 8% by weight. In another embodiment, the concentration of collagen in the collagen slurry, collagen suspension or an aqueous collagen solution range from about 4% to about 5% by weight.

In one embodiment, the collagen coating can be obtained by dipping the elastomeric matrix into a collagen slurry or collagen suspension and drying it under heat and/or vacuum to form a film coating. In one embodiment, the collagen coating can be obtained by dipping the elastomeric matrix into a collagen solution and drying it under heat and/or vacuum to form a film coating. In one embodiment, the collagen coating can be obtained by dipping the elastomeric matrix into a mixture of collagen slurry and solution and drying it under heat and/or vacuum to form a film coating.

In one embodiment, the collagen coating can be obtained by dipping the elastomeric matrix into a collagen slurry or collagen suspension and drying it under lyophilization conditions to form a lyophilized coating. In one embodiment, the collagen coating can be obtained by dipping the elastomeric matrix into a collagen solution and drying lyophilization conditions to form a lyophilized coating. In one embodiment, the collagen coating can be obtained by dipping the elastomeric matrix into a mixture of collagen suspension and solution and drying it under lyophilization conditions to form a lyophilized coating.

Optionally, the film or lyophilized collagen coating can be crosslinked to control the rate of in-vivo enzymatic degradation of the collagen coating and/or to control the ability of the collagen coating to bond to elastomeric matrix. The collagen can be crosslinked by methods known to those in the art, e.g., by heating in an evacuated chamber, by heating in a substantially moisture-free inert gas atmosphere, by bringing the collagen into contact with formaldehyde vapor, or by the use of glutaraldehyde. The cross-linking may comprise covalent cross-linking. In one embodiment, the film or lyophilized collagen coating can be crosslinked by bringing the collagen in contact with carboxyl-reactive chemical groups including carbodiimide compounds such as EDC (1-ethyl-3-(-3-dimethylaminopropyl) carbodiimide hydrochloride, and DCC (N',N'-dicyclohexyl carbodiimide).

Collagen pickup weights range from as low as 0.5 $\mu g/mm^3$ up to about 100 $\mu g/mm^3$. In one embodiment, collagen dosing levels range from about 5 $\mu g/mm^3$ up to about 10 $\mu g/mm^3$.

In one embodiment, the total ECM protein, such as collagen, loading within the scaffold is between about 0.01 and about 0.2 mg ECM protein/$mm^3$ scaffold. Alternatively, the total ECM protein, such as collagen, loading within the scaffold is between about 0.01 and about 0.1 mg ECM protein/$mm^3$ scaffold. Alternatively, the total ECM protein, such as collagen, loading within the scaffold is between about 0.02 and about 0.08 mg ECM protein/$mm^3$ scaffold. Alternatively, the total ECM protein, such as collagen, loading within the scaffold is between about 0.02 and about 0.05 mg ECM protein/$mm^3$ scaffold. In one embodiment, the total ECM protein, such as collagen, loading within the scaffold is about 0.04 mg ECM protein/$mm^3$.

In order to provide sufficient collagen coating on the scaffold, the collagen may be ground to a smaller particle size, for example by milling. The milling may comprise cryogenically grinding. In one embodiment, the collagen may be an average particle size of about 5 and about 100 $\mu m$. The collagen may be an average particle size of about 10 and about 20 $\mu m$. Alternatively, the collagen may have an average particle size of less than 50 $\mu m$. In another embodiment, the collagen may have an average particle size of less than 20 $\mu m$.

Design Configurations for Agents/Devices of the Invention

Agents or devices of the invention comprising a reticulated elastomeric matrix with a collagen coating can be readily fabricated in any desired size and shape. Such agents/devices are referred to herein with respect to the design configurations as implants. Suitable designs include, without limitation, those described in U.S. application Ser. No. 12/699,012 (U.S. Publication 2010/0318108 A1), the disclosures of which are hereby incorporated by reference. It is a benefit of the invention that the shape and configuration of elastomeric matrix may vary widely and can readily be adapted to desired anatomical morphologies.

The minimum dimension of the implant may be as little as 0.5 mm and the maximum dimension as much as 500 mm or even greater. In certain embodiments, the implant may be in any two-dimensional or three-dimensional shape. Exemplary embodiments of a two-dimensional shape may include regular and irregular shapes, such as, for example, triangular, rectangular, circular, oval, elliptical, trapezoidal, pentagonal, hexagonal and irregular configurations, including one that corresponds to the shape of the defect, and other shapes. Exemplary embodiments of a three-dimensional shape may include, plugs, cylinders, tubular structures, stent-like structures, and other configurations, including one that corresponds to the contours of the defect, and other configurations. The device may have a major axis having a length between about 2 cm to about 50 cm. The device may be in a square shape with a side having a length between about 2 cm to about 50 cm. In a preferred embodiment, it is contemplated that the implant would have a shape of a curved sheet with an oval configuration that optimally contours to the peritoneal cavity. In another embodiment, the implant would have a shape of a flat sheet with an oval configuration. The transverse or cross-sectional dimension of a curved or flat mesh configuration may range from as little as 0.5 mm to up to 10 mm. The length and width dimensions of the implant may range from as little as 10 mm to up to 500 mm. Optimally, such implants are dimensioned to allow for delivery using laparoscopic delivery methods by rolling, folding, or compressing such implant.

In another embodiment, the implant would have an elongated shape, such as the shapes of cylinders, rods, tubes or elongated prismatic forms, or a folded, coiled, helical or other more compact configuration. In an alternative embodiment, the implant of the invention may have a spherical, cubical, tetrahedral, toroidal, cup-like, or other form having no dimension substantially elongated when compared to any other dimension and with a diameter or other maximum dimension of from about 0.5 mm to about 500 mm.

For metastatic cell capture applications, it is an advantage of the invention that the implant can be effectively employed without any need to closely conform to the configuration of the application site, which may often be complex and difficult to model. Thus, in one embodiment, the implants have significantly different and simpler configurations which conformally fit the target site. Without being bound by any particular theory, the resilience and recoverable behavior that leads to such a conformal fit results in the formation of a tight boundary between the walls of the implantable device and the defect with substantially no clearance, thereby providing an interface conducive to the capture of metastatic tumor cells.

Furthermore, in one embodiment, the implantable device of the present invention, or implantable devices if more than one is used, should not completely fill the application site even when fully expanded in situ. In one embodiment, the fully expanded implantable device(s) of the present invention are smaller in a dimension than the application site and provide sufficient space within the application site to ensure vascularization, tumor cell capture, and proliferation, and for passage of blood to the implantable device. In another embodiment, the fully expanded implantable device(s) of the present invention are substantially the same in a dimension as the application site. In another embodiment, the fully expanded implantable device(s) of the present invention are larger in a dimension than the application site. In another embodiment, the fully expanded implantable device(s) of the present invention are smaller in volume than the application site. In another embodiment, the fully expanded implantable device(s) of the present invention are substantially the same volume as application site. In another embodiment, the fully expanded implantable device(s) of the present invention are larger in volume than the application site.

In embodiments of the invention, an optional anti-adhesion coating can be added. The coating can consist of biodegradable or biodurable polymeric materials. One embodiment of the invention incorporates a thin layer, coating or film of either a permanent polymer or biodegradable polymer used to reduce the potential for biological adhesions. In a preferred embodiment, a biodegradable or bioabsorbable coating is made from copolymers of caprolactone with lactic acid, glycolic acid, acid d-, l- and meso lactide and para-dioxanone. Compositions considered favorable for anti-adhesion properties include copolymers of caprolactone with lactic acid in the ratio of 40/60, 30/70 or 20/80 polycaprolactone to polylactic acid. This anti-adhesion film may be incorporated with the reticulated elastomeric matrix using various processing techniques known in the art including adhesive bonding, melt processing, compression molding, suturing, and other techniques.

Other embodiments involve implants for in-vivo delivery via catheter, endoscope, arthroscope, laparoscope, cystoscope, syringe or through non-endoscopic open procedures or other suitable delivery-device. In one embodiment, elastomeric matrices of the invention have sufficient resilience to allow substantial recovery, e.g., to at least about 30% of the size of the relaxed configuration in at least one dimension, after being compressed for implantation in the human body, In another embodiment, elastomeric matrices of the invention have sufficient resilience to allow recovery to at least about 60% of the size of the relaxed configuration in at least one dimension after being compressed for implantation in the human body. In another embodiment, elastomeric matrices of the invention have sufficient resilience to allow recovery to at least about 90% of the size of the relaxed configuration in at least one dimension after being compressed for implantation in the human body. In another embodiment, elastomeric matrices of the invention have sufficient resilience to allow recovery to at least about 95% of the size of the relaxed configuration in at least one dimension after being compressed for implantation in the human body.

Following delivery of the implant in-vivo, the device may be secured to the target area by any means. In one embodiment, the implant may be sutured to the target area. In another embodiment, the implant may be stapled in place. Other methods for fixation of the device include sutureless techniques such as fixation of the device with a glue (e.g., human fibrin glue).

There is provided a method of manufacturing an agent for modulating metastatic tumor cell dissemination, the method comprising the steps of:
preparing a suspended solution of an ECM protein;
coating the polycarbonate polyurethane matrix by saturation within the solution of the ECM protein; and
lyophilization of the ECM protein within the polycarbonate polyurethane matrix to form the agent for modulating metastatic tumor cell dissemination.

The ECM protein may be ground to (or provided in) a smaller particle size prior to coating. The grinding may be cryogenically grinding. The ECM protein may be ground to an average particle size of between about 1 and 100 microns. In another embodiment, the ECM protein may be ground to an average particle size of between about 5 and 50 microns. Alternatively, the ECM protein may be ground to an average particle size of between about 20 and 30 microns. The ECM protein may be ground to an average particle size of less than 100 microns. The ECM protein may be ground to an average particle size of less than 50 microns. The ECM protein may be ground to an average particle size of less than 20 microns.

Advantageously, the smaller average particle size facilitates the coating of a higher amount of ECM protein, such as collagen, relative to larger particle sizes. In particular large particles like fibrillary collagen can clog the matrix pores and reducing the particle size alleviates this problem. Cryogenically grinding the ECM protein can help to prevent denaturation.

The solution of ECM protein may be a solution of ECM protein and deionised water. The amount of ECM protein in solution may be between about 30 and about 80 mg ECM protein/g water. Alternatively, the amount of ECM protein in solution may be between about 35 and about 60 mg ECM protein/g water. The amount of ECM protein in solution may be between about 40 and about 50 mg ECM protein/g water.

The concentration of collagen in solution may range from about 0.05% to about 4.0% by weight. In another embodiment, the concentration of collagen in the collagen solution may range from about 0.1% to about 2.0% by weight. In another embodiment, the concentration of collagen in the collagen solution may range from about 0.2% to about 1.0% by weight. Alternatively, the concentration of collagen in the collagen solution may range from about 1% to about 10% by weight. In another embodiment, the concentration of collagen in the collagen solution may range from about 3% to about 8% by weight. In another embodiment, the concentration of collagen in the collagen solution may range from about 4% to about 5% by weight.

The polycarbonate polyurethane matrix may be saturated by repeated mechanical compressions under the surface of the ECM protein solution fluid.

The drying may be via a lyophilisation process that utilizes sublimation under vacuum after the material has been frozen, for example at less than −20° C. or less than −40° C.

The method may further comprise crosslinking the ECM protein, such as covalently crosslinking. Crosslinking may be provided by saturating the ECM protein in a solution of a molecule capable of covalently crosslinking the ECM protein, for example molecules comprising carboxyl-reactive chemical groups, such as 1-Ethyl-3-(3-dimethylamino-propyl)carbodiimide (EDAC). The lyophilisation process may be repeated after crosslinking.

The lyophilized ECM protein of the method may comprise or consist of collagen. The collagen may comprise or consist of Type I bovine collagen.

The present invention will be further described in more detail, by way of example only, with reference to the following figures in which:

FIG. 1—shows an agent of the invention comprising a reticulated scaffold coated with 6.36 µg collagen/mm³ scaffold and imaged by electron microscopy to show the reticulated scaffold from Biomerix (left panel; bar 500 µm), and the collagen fibers decorating the surface of the polymeric scaffold (middle panel at bar 25 µm; right panel at bar 10 µm).

Figure 2:
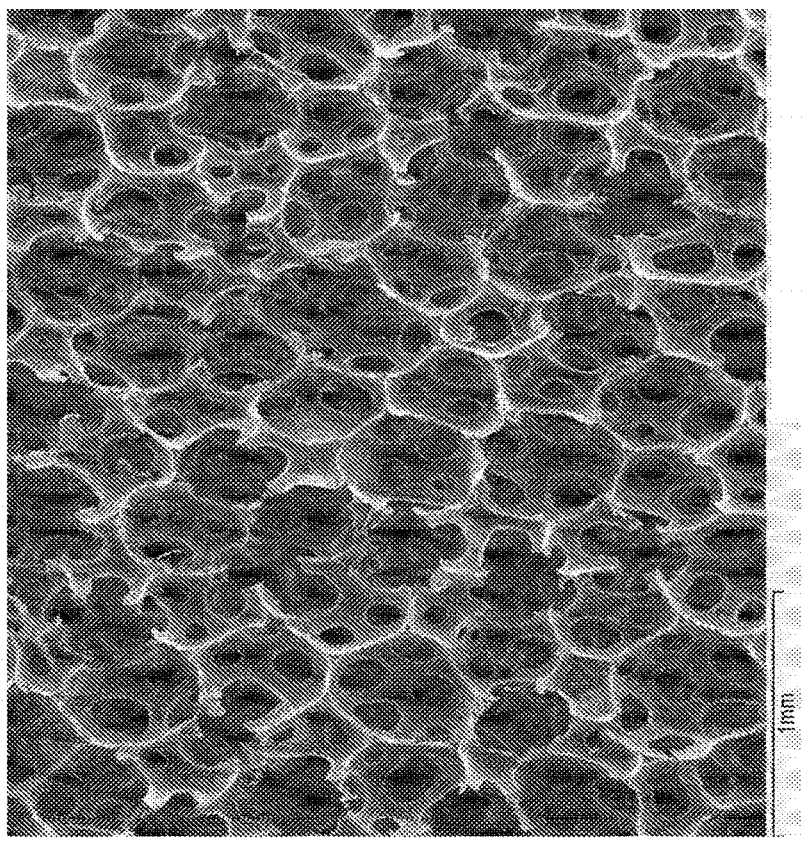

FIG. 2—shows the polycarbonate polyurethane scaffold and the open cell intercommunicating network present through the volume of the material. 35× magnification.

Figure 3:
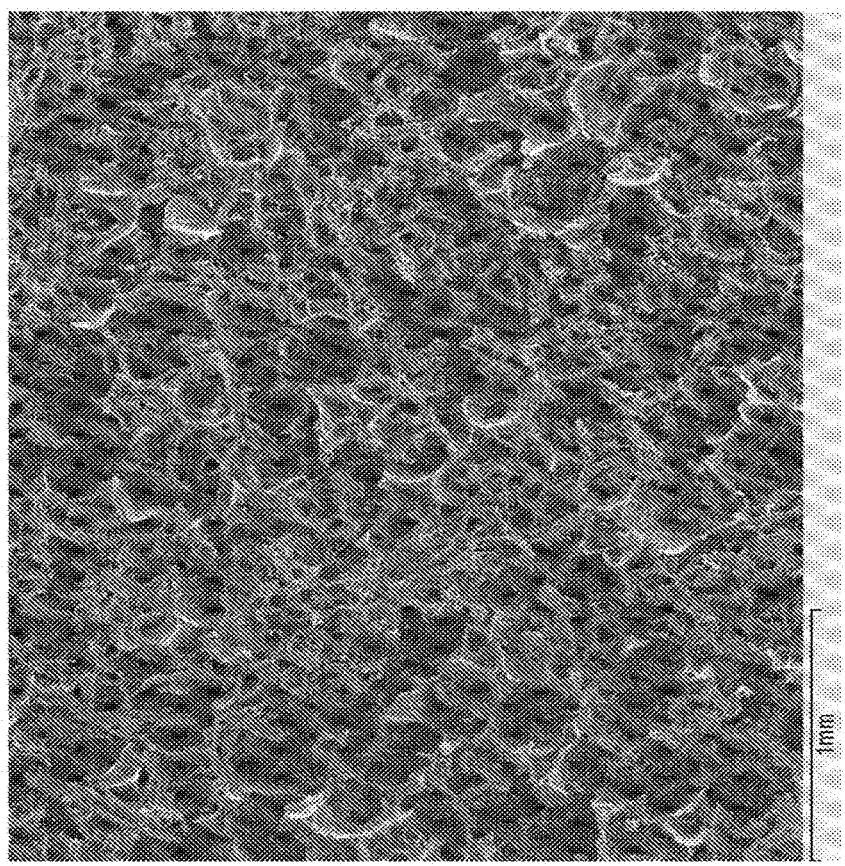

FIG. 3—shows the lyophilized collagen network (0.0400 mg/mm³ scaffold) distributed within the poycarbonate polymeric scaffold at 35× magnification.

Figure 4:
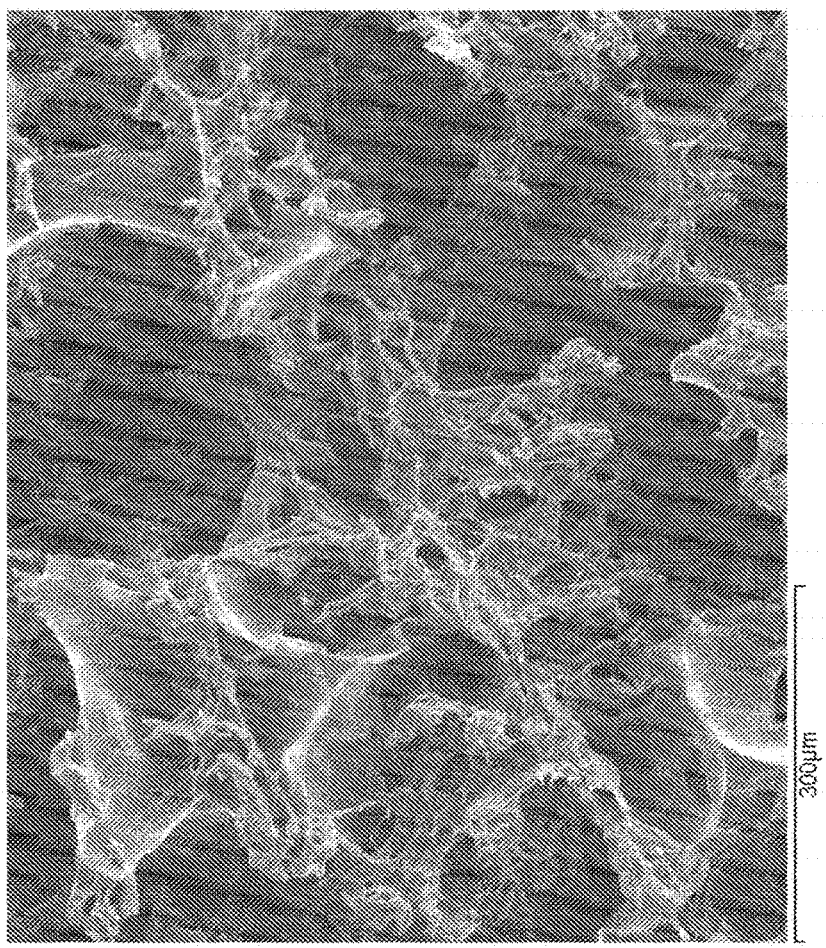

FIG. 4—shows the lyophilized collagen network distributed within the poycarbonate polymeric scaffold at 150× magnification.

Figure 5:
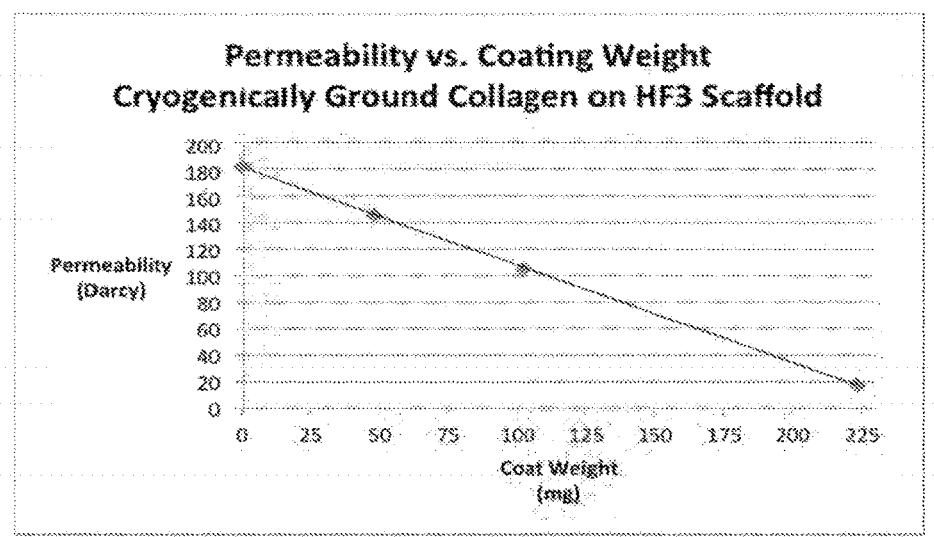

FIG. 5—shows the permeability of the composite material versus the total coat weight of collagen on the clinical size device.

FIG. 6A—shows attachment of fluorescent-labelled SKOV3 cells to the fibers of an agent of the invention, referred to herein as the M-Trap device, decorated with collagen (M-Trap) compared to the fibers of Biomerix scaffold without collagen (Scaffold). Attachment of the cells was facilitated by the orbital circulation of the tumor cells.

FIG. 6B—shows the capture of SKOV3 cell to an agent of the invention, wherein the agent comprises a 3D scaffold in the presence of collagen (M-Trap). The results show that cell capture was enhanced by the collagen coating compared to adhesion to the 3D scaffold without collagen (Scaffold). This enhancement was demonstrated in both a dose dependent manner with 25 and 250 µg collagen, and in a time-dependent manner for 24, 48 and 72 hours at 37° C. (p<0.001).

FIG. 7A—shows an increased capture of SKOV3 cells when cells were exposed to an enhanced adhesive surface.

FIG. 7B—shows the effect of exposure of fluorescent-labelled SKOV3 cells to the Biomerix scaffold coated with collagen (M-Trap) or to the Biomerix scaffold alone (Scaffold), in gradually increased 3D containers.

FIG. 7C—shows the effect of exposure of fluorescent-labelled SKOV3 cells to the Biomerix scaffold coated with collagen (M-Trap) located at the center (Scaffold 1) or at the exterior side (Scaffold 3) of the container, or at an intermediate location between them (Scaffold 2).

FIG. 7D—shows the reticulated scaffold coated with collagen (left panel D) and captured fluorescent SKOV3 cells within the scaffold (right panel D).

Figure 8:
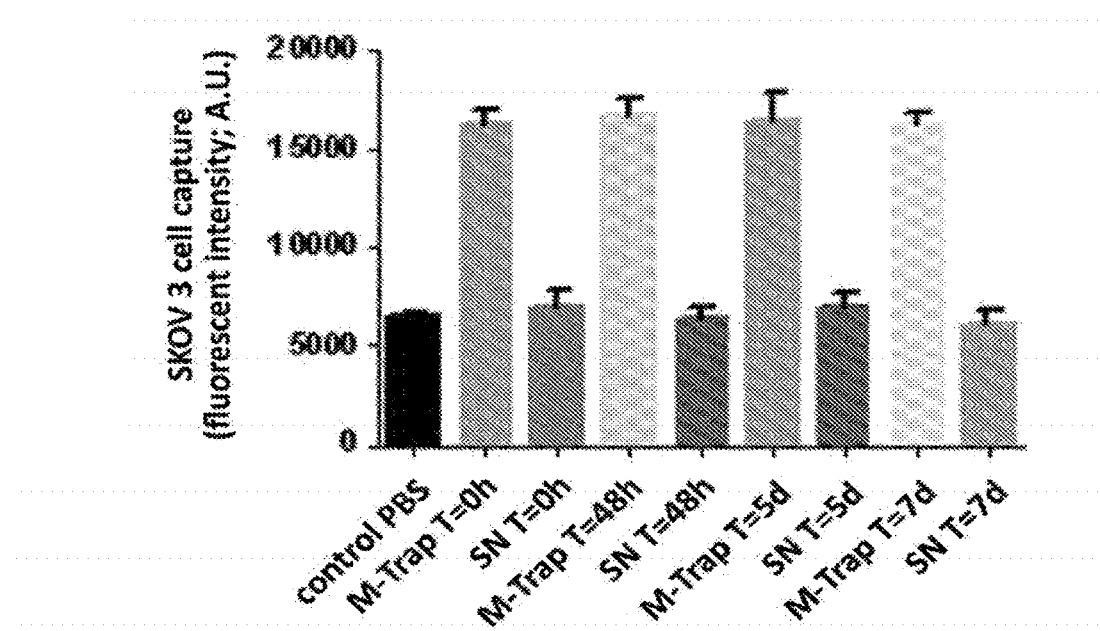

FIG. 8—shows adhesion assays to demonstrate the release of collagen from scaffolds following incubation in PBS for 0 hours, 48 hours, 5 days and 7 days.

Figure 9:
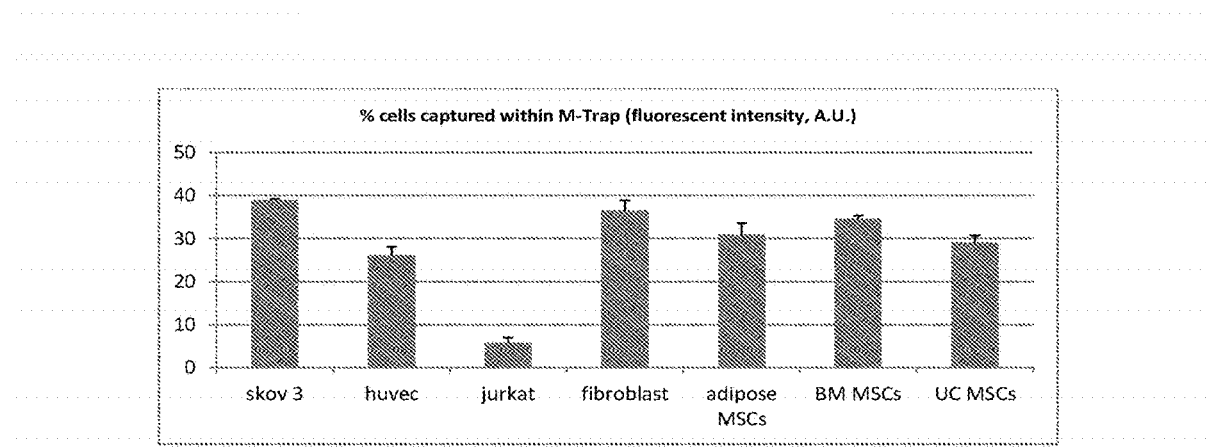

FIG. 9—shows the efficiency of M-trap for the capture of non-tumor cell types.

Figure 10:
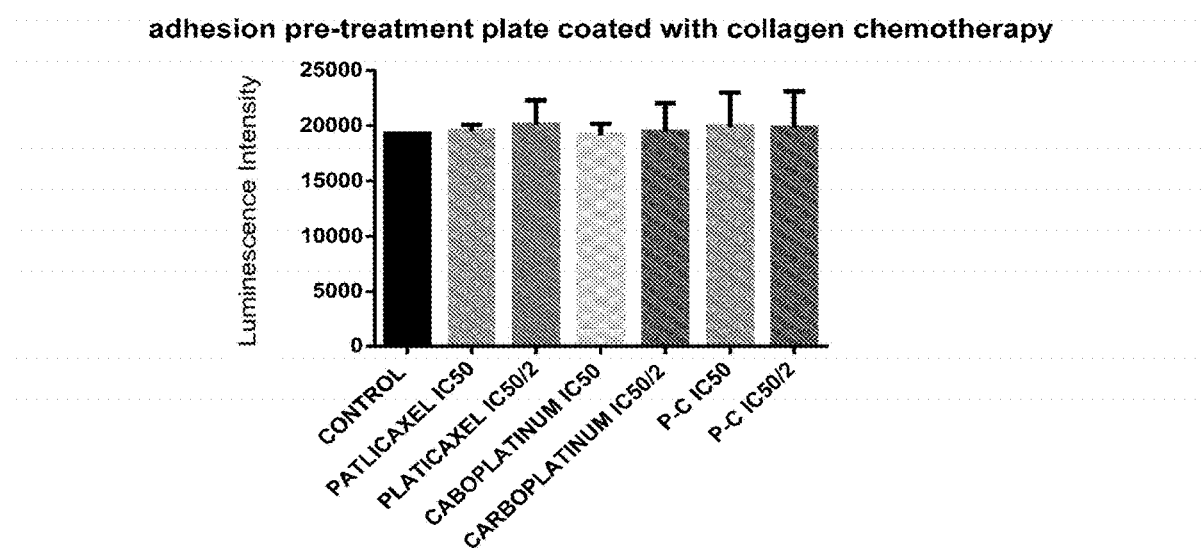

FIG. 10—shows short-term adhesion assays of SKOV3 cells labelled with calcein seeded in wells of a polystyrene plate with 5 µg/µl collagen. The coated surfaces were exposed overnight at 37° C. to 7 nM Paclitaxel as IC50 and to 3.5 nM Paclitaxel as IC50/2, to 10 µM Carboplatin as IC50 and to 5 µM Carboplatin as IC50/2, and to the combination of both Paclitaxel+Carboplatin at their respective IC50 (0.7 nM Paclitaxel, 1 µM Carboplatin) and IC50/2 (0.035 nM Paclitaxel; 0.5 µM Carboplatin) prior to seeding the cells.

Figure 11:
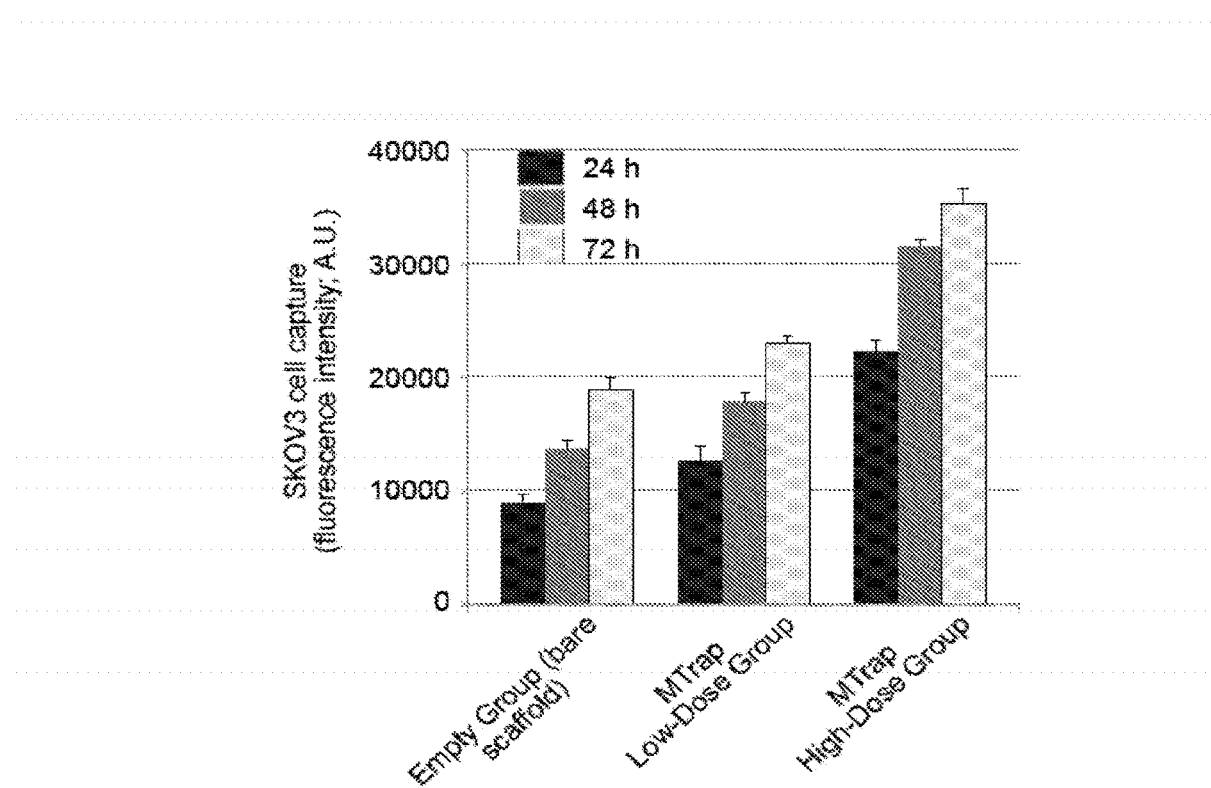

FIG. 11—shows the quantification of M-trap Tumor cell capture in a time and collagen concentration-dependent manner.

Figure 12:
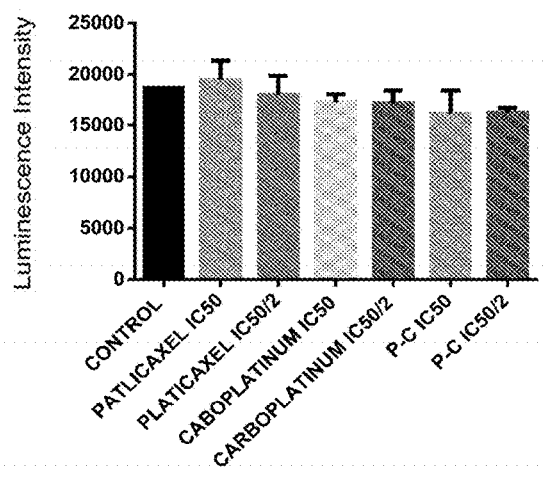

FIG. 12—shows short term adhesion assays of SKOV3 cells treated overnight at 37° C. with 7 nM Paclitaxel as IC50 and 3.5 nM Paclitaxel as IC50/2, 10 µM Carboplatin a IC50 and 5 µM Carboplatin as IC50/2, and the combination of both Paclitaxel+Carboplatin at their respective IC50 (0.7 nM Paclitaxel, 1 µM Carboplatin) and IC50/2 (0.35 nM Paclitaxol; 0.5 µM Carboplatin).

Figure 13:
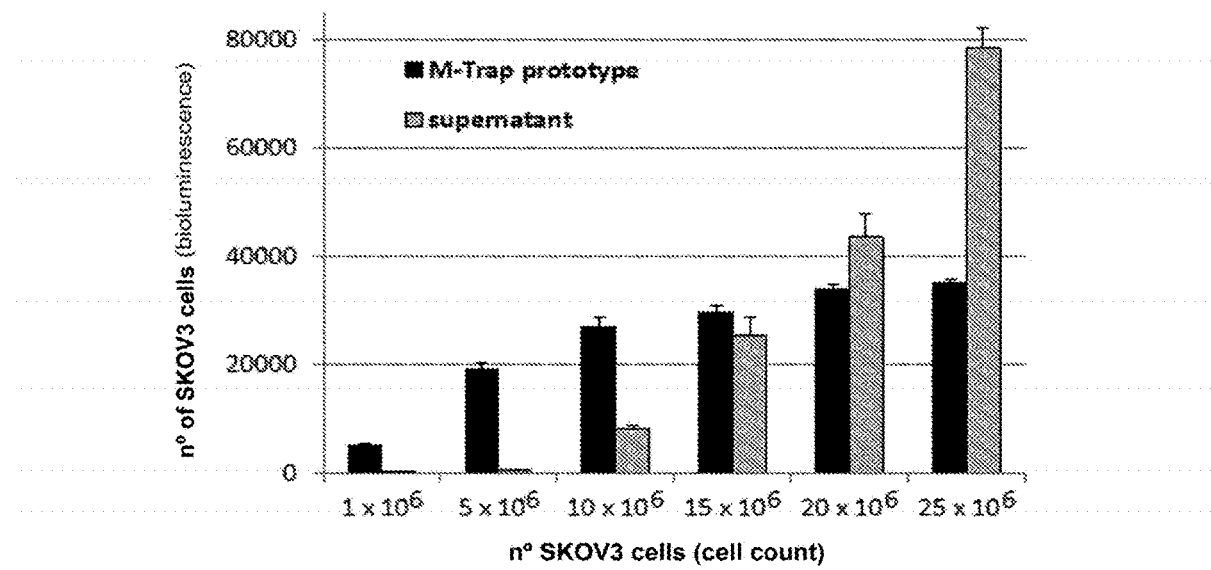

FIG. 13—shows the tumor cell saturation capacity of M-trap in an orbital adhesion assay.

FIG. 14A—shows peritoneal dissemination of SKOV3 cells stably expressing the luciferase reporter gene, following intraperitoneal injection in a mouse model of ovarian cancer.

FIG. 14B—shows the location of the device when surgically implanted at the inner wall of the peritoneum opposite to the natural sites of metastasis, one week before SKOV3 cell injection.

Figure 15:
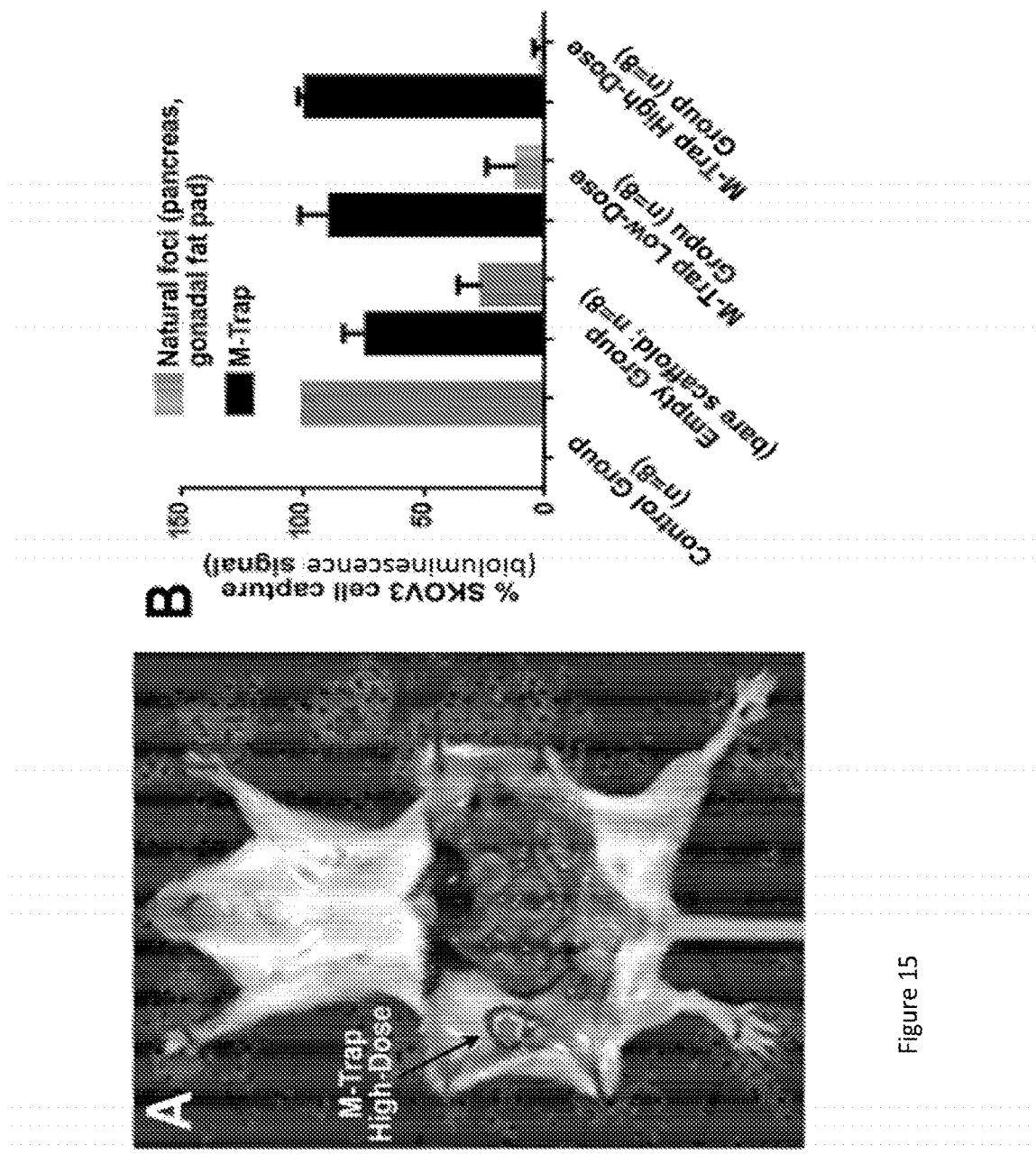

FIG. 15A—shows the complete remodelling of the peritoneal pattern of metastasis by M-Trap device, this representative image showing a complete capture of tumor cells within M-Trap device and a complete eradication of metastasis at natural sites.

FIG. 15B—quantification of the amount of tumor cells at natural sites and at M-Trap device with increased amounts of collagen. This quantification also demonstrates that the main capture action of the device is provided by the scaffold, the collagen coating auxiliary improving the capture efficiency.

FIG. 16A—shows the incomplete efficacy of a pharmacological mode of action technology (pluronic+EGF) to capture tumor cells disseminating into the peritoneal cavity.

Controlled release of EGF as chemoattractant was not as efficient as M-Trap device to completely capture metastatic cells.

FIG. 16B—shows the incomplete efficacy of another pharmacological mode of action technology (PLGA+EGF) to capture tumor cells disseminating into the peritoneal cavity. Controlled release of EGF as chemoattractant was not as efficient as M-Trap device to completely capture metastatic cells.

Figure 17:
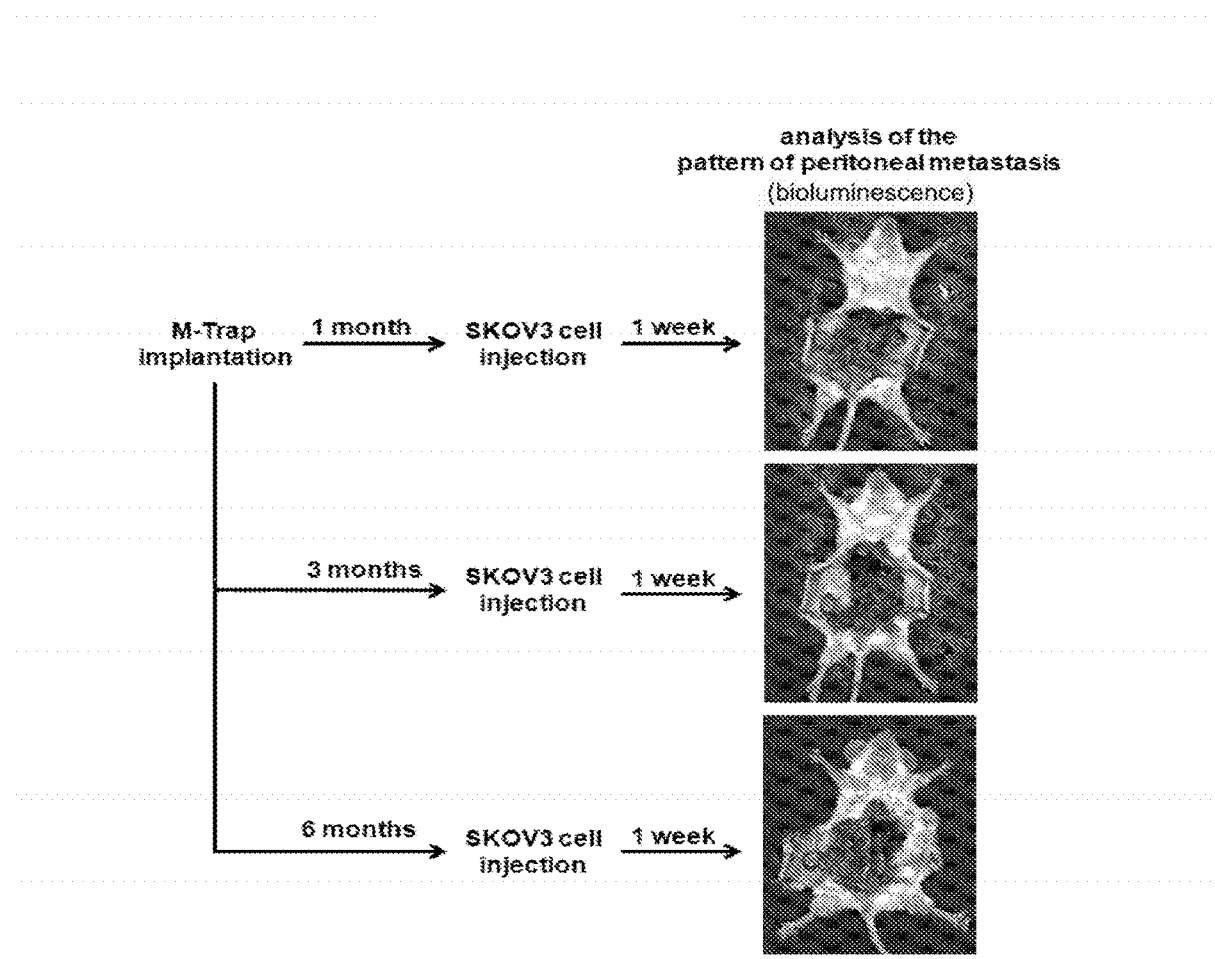

FIG. 17—shows the efficiency of the M-trap device which captured all metastatic cells at each time point, one, three and six months post-implantation in an in vivo model of metastatic ovarian peritoneal dissemination.

Figure 18:
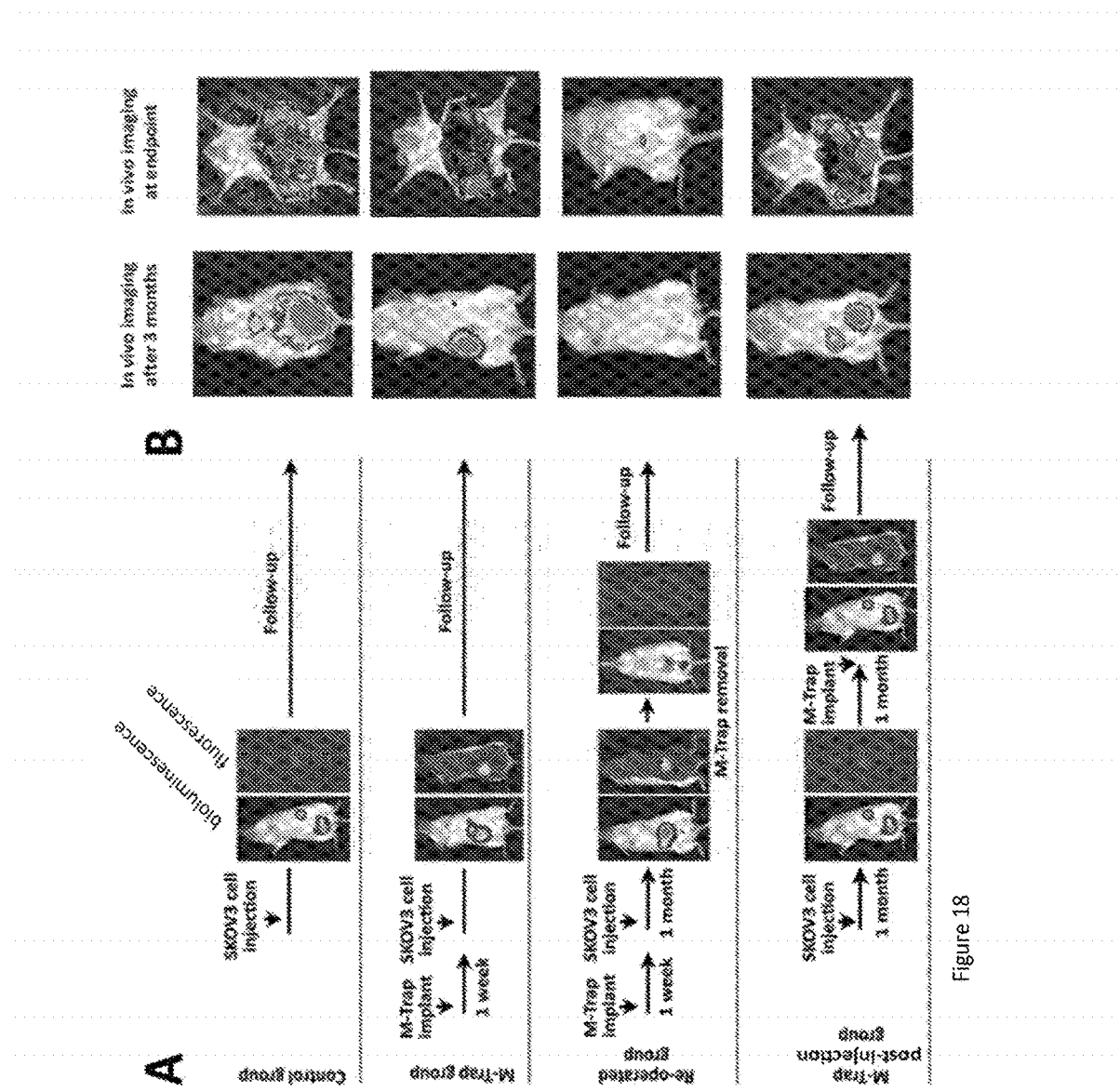
Figure 18:
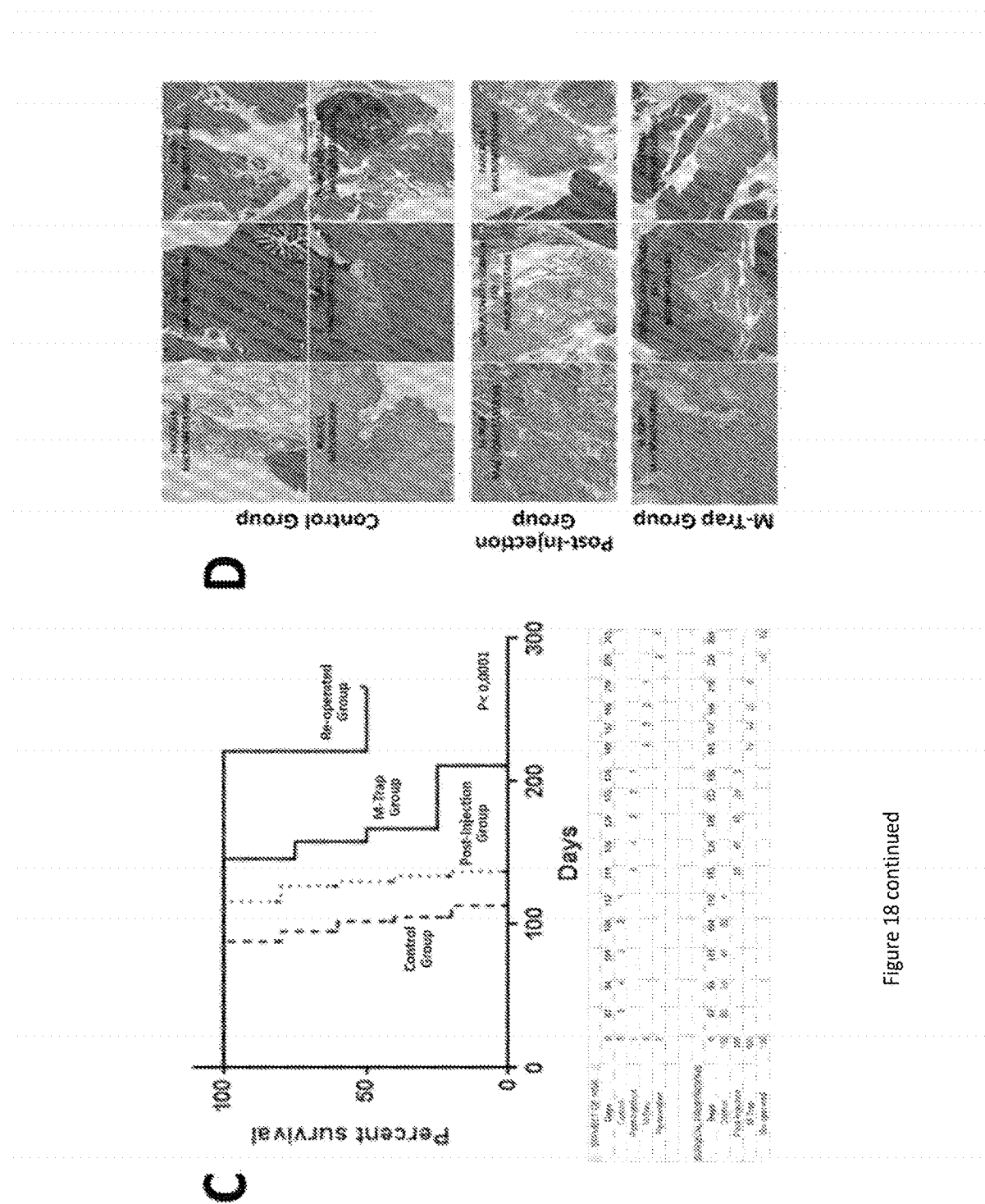

FIG. 18A—schematic description of the four arms included in the preclinical trial demonstrating M-Trap benefit in survival in the mice model of ovarian peritoneal metastasis.

FIG. 18B—in vivo follow-up of the pattern of peritoneal dissemination for each of the four arms included in the preclinical trial. Biolumiscence imaging of tumor cell implants in the peritoneal cavity three months after SKOV3 cells and at sacrifice shows an effective focalization of the disease in the presence of M-Trap device, implanted both pre- and post-injection, in comparison to the massive peritoneal dissemination shown in the control arm. Finally, removal of M-Trap device upon capture completely eradicates the peritoneal disease.

FIG. 18C—Kaplan-Meyer survival curve demonstrates the benefit in survival by the presence of M-Trap device. Focalization of the disease both before (M-Trap group) and after (Post-injection group) natural metastasis formation, resulted in an improved survival. Removal of M-Trap upon capture (Re-operated group) further impacted in survival ($p<0.001$).

FIG. 18D—Histological examination of organs and mesothelium at sacrifice confirmed the reduced peritoneal extension of the disease in the presence of M-Trap device. Representative images of affected organs for each group included in the preclinical study are shown.

Figure 19:
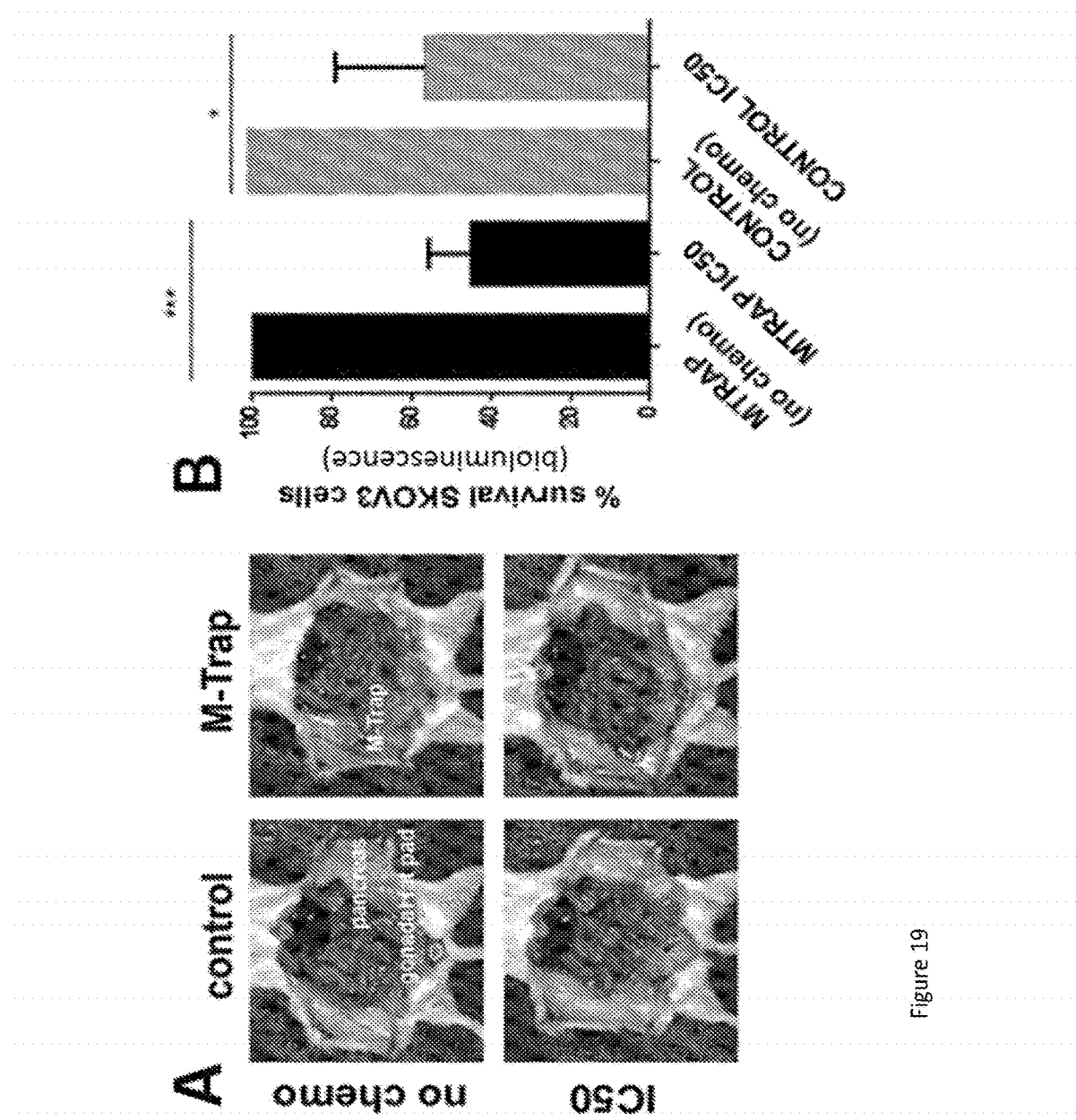

FIG. 19A—shows representative images demonstrating that the efficacy of M-Trap device to completely capture tumor cells disseminating in the peritoneal cavity is not impaired by the presence of IC50 concentrations of standard chemotherapy in ovarian cancer (carboplatin-paclitaxel).

FIG. 19B—shows the quantification of tumor cell survival to standard peritoneal chemotherapy in the presence or not of M-Trap device.

Figure 20:
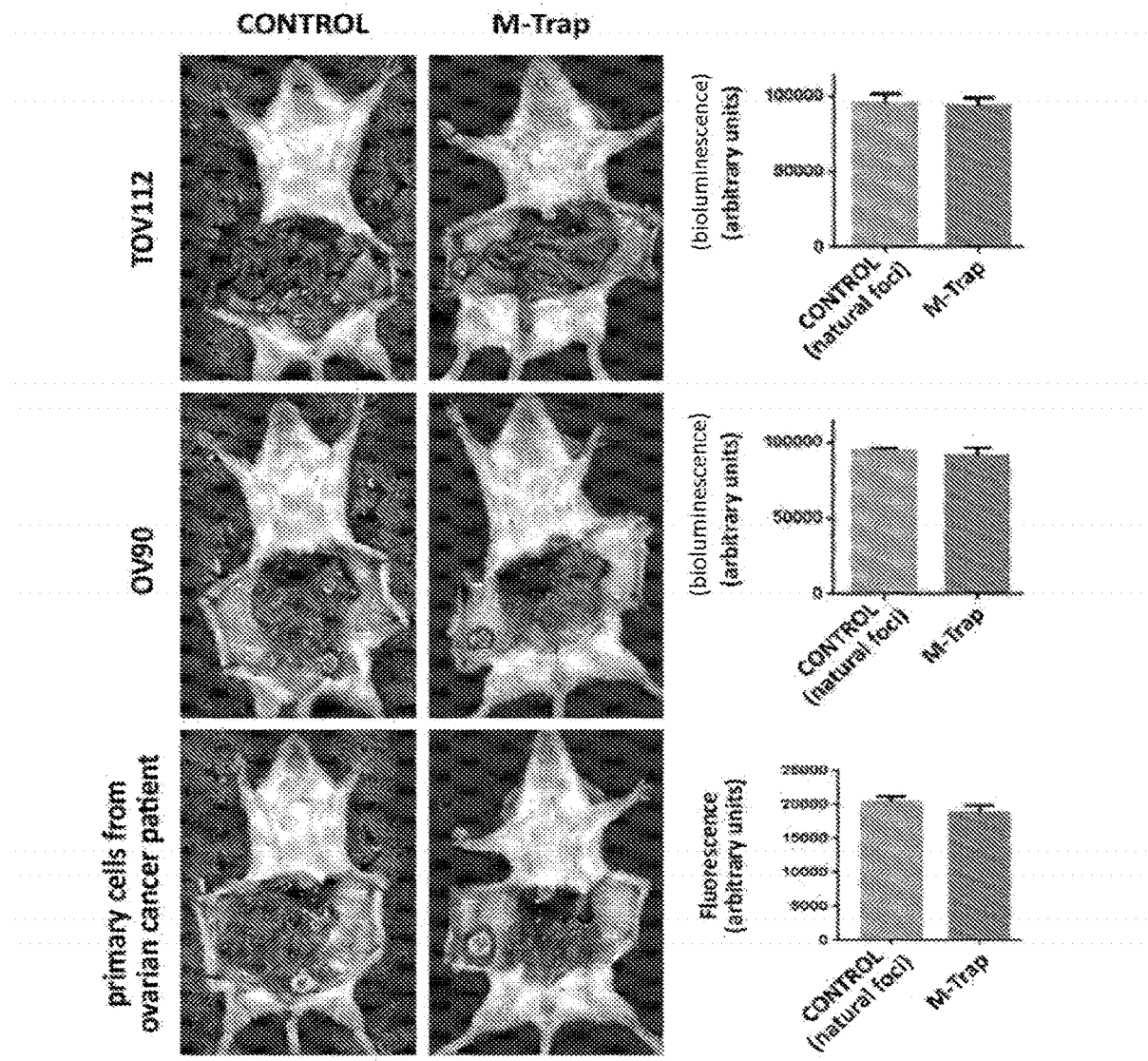

FIG. 20—shows representative images of the pattern of peritoneal metastasis in the presence or not of M-Trap devices, for different clinically relevant ovarian cancer cell lines (serous TOV112; endometroid OV90; and primary cancer cells isolated from ascitic fluid of ovarian cancer patients). Histograms show quantification of the amount of different ovarian tumor cells at natural sites and captured by M-Trap device, further demonstrating the universality of M-Trap technology.

Figure 21:
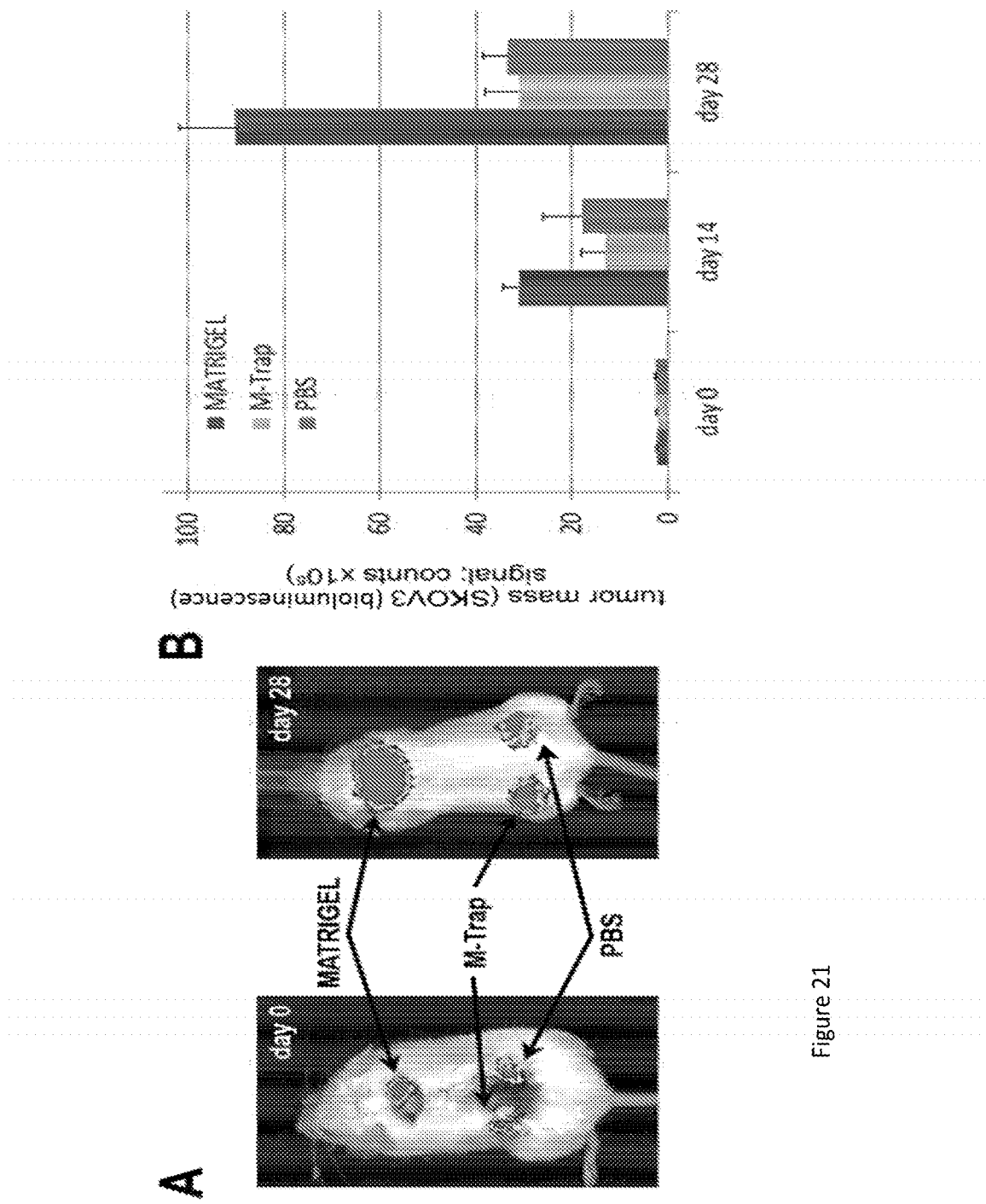

FIG. 21A—shows a comparative in-vivo assay in which subcutaneous SKOV3 cell tumors were generated in mice under three different conditions (PBS, Matrigel, M-trap) with quantification of the bioluminescence at 2 weeks and 4 weeks to assess tumor growth and proliferation.

FIG. 21B—shows how M-trap does not contribute to tumor growth upon cell capture in a murine subcutaneous tumor model.

FIG. 22A—shows Increasing concentrations of fibronectin decorating the scaffold were able to capture SKOV3 cells in the in vitro dynamic orbital assay mimicking transcoelomic peritoneal flow, in a dose dependent manner.

FIGS. 22B and 22C—show fibronectin coating of Biomerix scaffold resulted in a complete remodeled pattern of peritoneal implants in the in vivo model of ovarian dissemination, with almost all metastatic tumor cells being captured within the device.

EXAMPLES

Trap Device

Trap devices of the invention, comprising an agent for modulating metastatic tumor cell dissemination for use in the treatment and/or prevention of a metastatic cancer wherein the agent for modulating metastatic tumor cell dissemination is an extracellular matrix (ECM) protein carried on a reticulated elastomeric matrix, preferably a polycarbonate polyurethane urea matrix, are manufactured by coating the matrix with the ECM protein. Methods of production of the matrix are known to the skilled person and are described, for example in issued U.S. Pat. No. 7,803,395 and U.S. Pat. No. 8,337,487 (the contents of which are incorporated in their entirety, by reference).

The polycarbonate polyurethane urea matrix of the Examples (sometimes referred to as the Biomerix scaffold) is a non-resorbable, reticulated, cross-linked, polycarbonate polyurethane-urea matrix (Biomerix, Fremont, Calif., USA) offering a fully interconnected, highly permeable, macroporous morphology with over 90-95% void content. The material specifications are provided in Table 1. The scaffold was coated with 250 µg collagen and imaged by electron microscopy. The results are shown in FIG. 1.

TABLE 1

| Biomerix HF3 Formulation, Material Specifications | |
|---|---|
| Property | Requirement |
| Permeability | >250 Darcy |
| Average cell size | <385 µm |
| Density | 3.5-3.9 lb/ft$^3$ |
| Compressive strength | 1.0-1.8 psi |
| Tensile strength parallel | ≥50 psi |
| Elongation parallel | >180% |
| Tensile strength perpendicular | ≥36 psi |
| Elongation perpendicular | >180% |

The Biomerix scaffold permits in-growth and proliferation of host cells and tissue into the volume of the polymeric scaffold. The polymeric scaffold can be characterized as an open and interconnected network of polycarbonate polyurethane which forms a three-dimensional spatial structure with a high void volume and surface area. The material can be further characterized as having an elastomeric nature that enables it to be compressible, resilient and demonstrating good recovery properties after compression or manipulation. The reticulated elastomeric matrix is comprised of a biodurable and biocompatible polymer that will not degrade or change in properties after implantation within the body for the lifetime of the device. FIG. 2 shows the polycarbonate scaffold and the open cell intercommunicating network that is present through the volume of the material.

Methods to coat the scaffold with collagen are described above.

Collagen coated polycarbonate polyurethane urea matrices are also referred to herein as M-traps.

The collagen component of the M-trap device is comprised of a fibrillar Type I bovine collagen that is lyophilized onto the reticulated elastomeric polycarbonate polyurethane scaffold via a manufacturing process that ensures that the collagen network permeates through the entirety of the polymeric scaffold. The bovine fibrillar collagen is sourced from Maquet/Datascope. The collagen is crosslinked after lyophilization to improve the durability of the collagen such that it will remain intact and effective for the intended life of the device. The lyophilized collagen network has a high permeability and surface area similar to the polymeric scaffold and as such it does not restrict in-growth and proliferation of host cells and tissue into the volume. The collagen within the polymeric scaffold acts as an attractant to the disseminating tumor cells within the cavity. FIGS. 3 and 4 show the lyophilized collagen network distributed within the polycarbonate polymeric scaffold at different magnifications.

M-Trap Device Configuration and Optimized Collagen Coating Concentration

The clinical M-Trap device was configured as a flat sheet of the composite material with a thickness of 5 mm and an oval shape with a major axis of 50 mm and a minor axis of 15 mm. The total collagen loading within the scaffold for the clinical devices was approximately 0.04 mg collagen/mm$^3$ for a total delivered amount of collagen of approximately 120 mg of type I bovine collagen per device. A range of sizes of the M-Trap device can also be provided, where the equivalent collagen amounts may be scaled up or down appropriately.

Initial Collagen Concentration Optimization Experiments

Initial conceptual development of the M-trap device utilized a soluble form of rat tail collagen as the cancer cell attractant at a dose level of 6.36 μg/mm$^3$ of scaffold. The initial development work on the clinical device investigated whether it was possible to increase the dose level of collagen as the attractant for additional cell capture. Utilizing a soluble collagen material was found to limit the amount of collagen that could be applied to the scaffold as the saturated solution concentration of collagen was a limiting factor. To address this issue, fibrillar bovine type I collagen was utilized as this biomaterial has multiple regulatory clearances within medical devices. Coating of the scaffold with a fibrillar material was found to be initially ineffective since the length of the fibrils were greater than the openings within the polymeric scaffold and the collagen was not able to be uniformly distributed through the interior of the scaffold. The collagen was cryogenically ground within an oscillatory ball mill to reduce the mean particle size to approximately 10-20 m. Cryogenic grinding was chosen over standard ball milling of the collagen to ensure that the proteins of the collagen were not denatured.

Utilizing the cryogenically ground microparticles of the bovine collagen, solutions of various concentrations were produced and coated on the scaffold by a film coating and also by a lypholization processes. The lyophilized process had an advantageous morphology at the microscopic level of additional surface area for cellular adhesion within the scaffold and was determined to be the preferred method of combining the scaffold and collagen. To determine the maximum amount of collagen that could be placed within the scaffold and still maintain device functionality, experiments were conducting looking at the permeability of the resulting composite material versus the total coat weight of collagen on the clinical size device. The results of these experiments are presented in FIG. 5. t was determined that a high dose level of 0.0400 mg/mm$^3$ and a low dose level of 0.0067 mg/mm$^3$ would be investigated further within the preclinical models. The preclinical size of the M-Trap device is 6 mm×3 mm×2 mm. Preclinical testing demonstrated that the optimized collagen concentration for M-trap is the high dose level of collagen of 0.0400 mg/mm$^3$.

M-Trap Manufacturing Process

A uniform collagen coating within the polymeric scaffold was achieved by saturation of a suspension of the cryogenically ground collagen with an approximate particulate size of 10-20 microns, and deionized water within the scaffold. The primary control of the amount of collagen left behind on the surface of the scaffold is the initial concentration of the collagen within the suspension and subsequent complete saturation of the sponges prior to the drying process. To determine the amount of collagen within the solution needed, the amount of suspension that can be held within the scaffold must first be understood. The polymeric scaffold is a hydrophobic polycarbonate polyurethane porous polymer that will not readily adsorb water onto the surface of the material. However, it will readily absorb and hold water within the fine, open structure of the material once saturated due to surface tension. Based on multiple experiments, the total solution contained within the scaffold at saturation is 0.00086 g/mm$^3$ Scaffold.

Based on the optimized (high dose) amount of collagen desired, a solution concentration of 46.5 mg Collagen/g H$_2$O was made and maintained under constant stirring prior to coating the scaffolds. To accomplish the saturation of the scaffold, the material was repeatedly mechanically compressed under the surface of the fluid to remove any entrained air and filled with suspension. Saturated scaffolds were placed onto a porous substrate after being coated so that a flat liquid boundary layer is not created at the surface of the scaffold prior to drying. The water was removed from the solution within the scaffold via a lypholization process that utilizes sublimation under vacuum after the material has been frozen to −45° C.

To enable the collagen within the scaffold to have a greater efficacy over time in-vivo, the collagen within the scaffold was crosslinked by saturating the lyophilized composite scaffolds in a 100 mM solution of 1-Ethyl-3-(3-dimethylaminopropyl)carbodiimide (EDAC) and repeating the lyophilization process an additional time.

M-Trap Technology Acts as a Preferential Niche for Implantation and Efficiently Captures Peritoneal Metastatic Cells.

Figure 6:
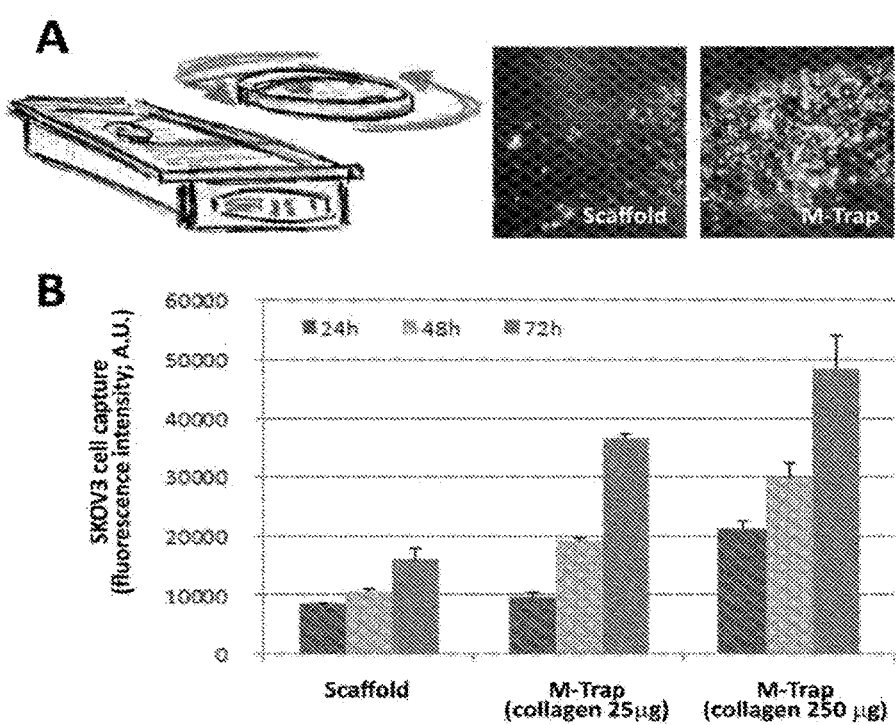

To analyze the mode of action of M-Trap devices, with collagen fibers at the surface of the non-degradable 3D scaffold, a in vitro assay was developed aiming to mimic the natural flow of peritoneal fluid within the abdominal cavity directed by gravity to its most dependent sites and providing a route for the transcoelomic dissemination of detached tumour cells (Tan at al, 2006). For this, the capture of 250,000 calcein-labelled SKOV3 cells re-suspended in a 2 ml volume to the M-Trap device located in a P6 cell culture plate (3.5 cm diameter) subjected to an orbital movement of 90 rpm was evaluated. Attachment of fluorescent-labelled SKOV3 cells to the fibers of the M-Trap device decorated with collagen (M-Trap) compared to the fibers of Biomerix scaffold without collagen (Scaffold) was further facilitated by the orbital circulation of tumor cells (FIG. 6, panel A), close to the clinical scenario of metastatic dissemination within a peritoneal cavity. Under these dynamic conditions, the capture of SKOV3 cells to the 3D scaffold in the presence of collagen (M-Trap) was enhanced compared to adhesion to the 3D scaffold without collagen (Scaffold) both in a dose dependent manner with 25 and 250 mg collagen, and in a time-dependent manner for 24, 48 and 72 hours at 37° C. (p<0.001; FIG. 6 panel B), further indicative of the specificity of SKOV3 cells attachment to M-Trap due to the adhesive ability of collagen as a capture agent. These in vitro results demonstrate that an M-Trap device composed of the Biomerix scaffold (polycarbonate polyurethane cross linked with urea) coated with collagen might be acting through a non-pharmacological mode of action by providing a favored surface for the adhesion of tumor cells that are orbital circulating within a 3D container; translated to the clinics, M-Trap device may be competing with the natural sites of peritoneal implantation and supporting a preferential niche for the attachment and capture of metastatic tumor cells.

Figure 7:
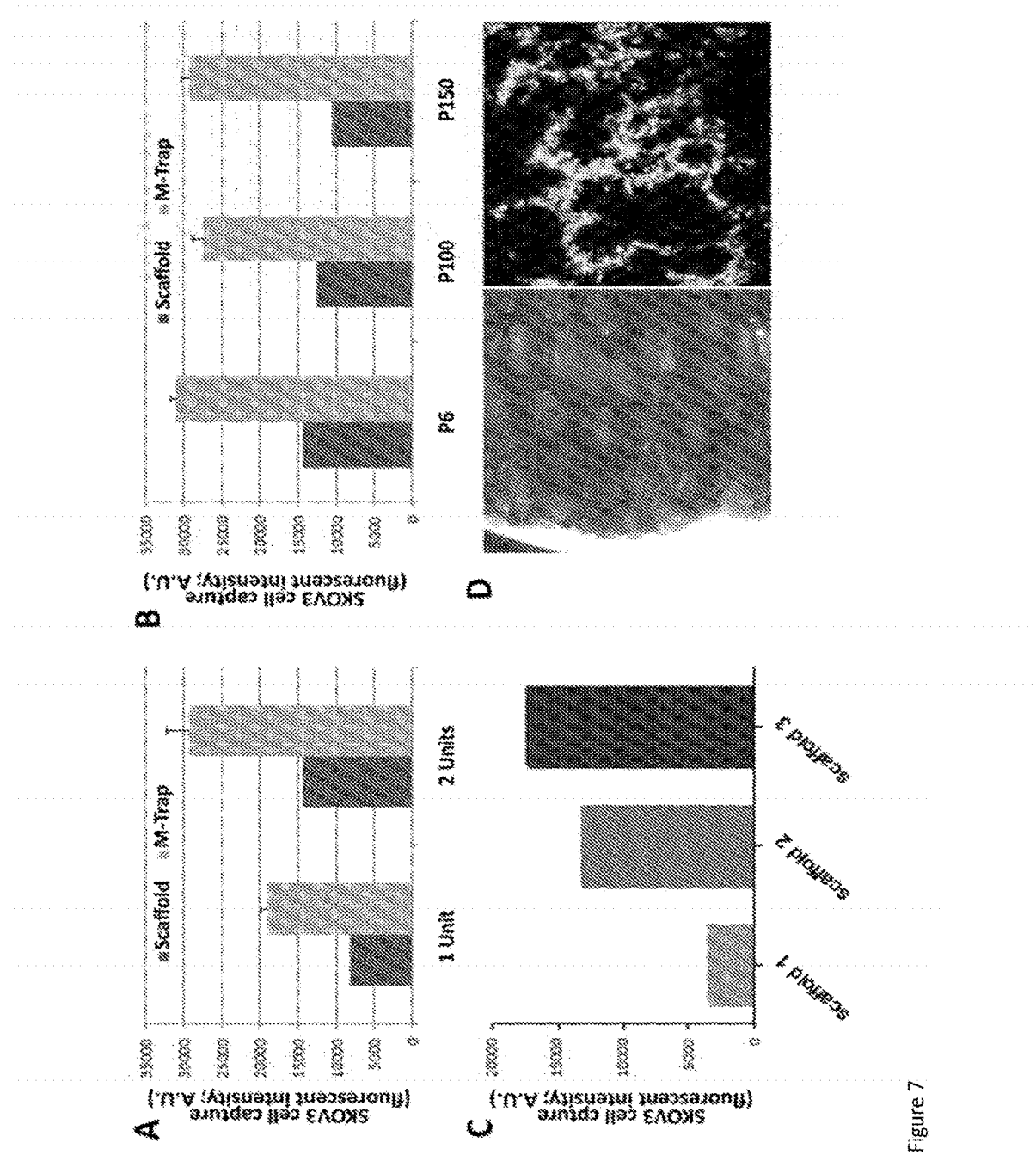

To further confirm the non-pharmaological mode of action of the M-Trap device composed by the Biomerix scaffold coated with collagen, the dynamic capture of calcein-labelled SKOV3 cells when exposed to a increased surface of M-Trap device during 24 hours at 37° C. was evaluated. For this, the ability of one or two units of the Biomerix scaffold without collagen (Scaffold) or with collagen (M-Trap), to capture SKOV3 cells in the dynamic assay mimicking peritoneal dissemination was compared. As shown in FIG. 7 panel A, an increased capture of SKOV3 cells was evidenced when cells were exposed to an enhanced adhesive surface. Likewise, when fluorescent-labelled SKOV3 cells were exposed to the Biomerix scaffold coated with collaged (M-Trap) or just to the scaffold (Scaffold), in gradually increased 3D containers (P6 corresponding to a 3.5 cm diameter cell culture plate; P100 corresponding to a 8.5 cm diameter cell culture plate; and P150 corresponding to a 13.5 cm diameter cell culture plate), no significant differences in the efficiency of SKOV3 cells capture (FIG. 7, panel B) was observed, further indicative of a non-pharmacological mode of action of the M-Trap technology of the invention. Finally, when the fluorescent-labeled SKOV3 cells were exposed to the Biomerix scaffold coated with collagen (M-Trap) located at the center (Scaffold 1) or at the exterior side (Scaffold 3) of the container, or at an intermediate location between them (Scaffold 2), a increased ability to capture SKOV3 dells was observed corresponding to the heterogeneous distribution of SKOV3 cells in the solution subjected to an orbital movement during 24 hours (FIG. 7, panel C). The capture of SKOV3 cells within the M-Trap composed of the Biomerix scaffold coated with collagen was further confirmed by fluorescent microscopy. Images show the reticulated scaffold coated with collagen (FIG. 7, left panel D) and captured fluorescent SKOV3 cells within the scaffold (FIG. 7, right panel D). In addition to reinforcing the non-pharmacological mode of action of M-Trap composed of the Biomerix reticulated scaffold (polycarbonate polyurethane urea matrix) coated with collagen, these results also demonstrate that the translation of M-Trap device into the clinics is not limited by the scaling of M-Trap dimensions to the peritoneal cavity, and must be accompanied by a re-dimension of M-Trap to an optimal size that might balance the maximal surface of the device with a minimal impact at the peritoneum (i.e. avoiding intestinal adherences).

The stability of the M-Trap device composed of the Biomerix scaffold coated with collagen was evaluated through a release experiment combined with a short term adhesion assay. Briefly, we incubated the M-Trap device in 100 µl of PBS for 0 hours, 48 hours, 5 days and 7 days. At the indicated times, the supernatant was recovered with the potential collagen traces released from the scaffolds. A short-term adhesion assay as described was then performed with both the scaffolds (M-Trap) and their corresponding supernatants (SN). As can be observed (FIG. 8), no difference could be found among scaffolds or among supernatants along incubated times, as well as between supernatants and control basal adhesion in PBS conditions. These results are indicative that no release of collagen occurred during incubation of M-Trap devices and demonstrating the stability of M-Trap technology at least for the indicated times.

M-Trap Technology Efficiently Captures Additional Cell Types with Adhesive Abilities Disseminating in the Peritoneal Cavity.

The universality of M-Trap technology to capture additional types of cells with adhesive abilities disseminating in the peritoneal cavity may beneficially impact on the efficacy of M-Trap by generating a more clinically relevant niche to compete with the natural sites of implantation of tumor cells disseminating in the peritoneum. The efficiency of the polycarbonate polyurethane scaffold with collagen coated M-Trap prototype to capture different types of cells was evaluated in the dynamic in-vitro capture assay with the M-Trap prototype placed in a P6 well plate and fluorescent-labelled cells added in suspension and incubated under orbital movement for 24 hours. Quantification of the percentage of cells captured by M-Trap relative to the cells in suspension at the end of the experiment as shown in FIG. 9. Cell types evaluated include the ovarian cancer cell line SKOV3, HUVEC endothelial cells, JURKAT lymphocytes, fibroblasts and mesenchymal stem cells of adipose, bone marrow (BM MSC) and umbilical cord (UC MSC) origin. These cell types are representative of the cell types present in the peritoneal cavity which could be interacting with the implanted M-Trap device. As can be observed, the efficiency of cell capture correlates with the capacity of these cells to attach to solid surfaces, with tumor cells, fibroblasts, MSC and endothelial cells being efficiently captured as they adhere rapidly to adhesive surfaces. In contrast, lymphocytes do not efficiently adhere to solid surfaces, and in fact, they grow in suspension. These results reinforce the non-pharmacological mode of action of M-Trap, without any active selection of cells but a passive adhesive affect for the capture of cells disseminating into the peritoneal cavity.

Impact of Chemotherapy on the Efficacy of M-Trap Device

The adhesion of SKOV3 cells in the presence or not of the standard therapy used in ovarian cancer (Paclitaxel+Carboplatin) was evaluated.

The impact of chemotherapy on the adhesive properties of a polymeric surface coated with collagen and the impact on the adhesive properties of tumor cells, exposed to the IC50 concentration of both drugs individually and in combination, were evaluated separately. For the impact of chemotherapy on the adhesive properties of the material, the bottom of a polystyrene well plate was coated with 5 µg/µl collagen during overnight at a 37° C. The coated surface was exposed overnight at 37° C. to 7 nM Paclitaxel as IC50 and to 3.5 nM Paclitaxel as IC50/2, to 10 µM Carboplatin as IC50 and to 5 µM Carboplatin as IC50/2, and to the combination of both Paclitaxel+Carboplatin at their respective IC50 (0.7 nM Paclitaxel, 1 µM Carboplatin) and IC50/2 (0.35 nM Paclitaxel; 0.5 µM Carboplatin). Finally a short-term adhesion assay was performed with $50 \times 10^4$ SKOV3 cells labeled with calcein seeded in the different treated well plates for 1 hour before washing and quantification of adhered cells with a luminometer. As shown in FIG. 10, no significant differences in SKOV3 cell adhesion were observed when the polymeric surface cored with collagen was exposed to the different chemotherapy conditions.

With reference to FIG. 12, the impact of chemotherapy on the adhesive ability of SKOV3 cells was also evaluated. For this, SKOV3 cells were treated overnight at 37° C. with 7 nM Paclitaxel as IC50 and 3.5 nM Paclitaxel as IC50/2, 10 µM Carboplatin as IC50 and 5 µM Carboplatin as IC50/2, and the combination of both Paclitaxel+Carboplatin at their respective IC50 (0.7 nM Paclitaxel, 1 µM Carboplatin) and IC50/2 (0.35 nM Paclitaxel, 0.5 µM Carboplatin). A short-term adhesion assay was than performed to un-treated collagen coated well plates as described, and a slightly diminished capacity of SKOV3 cells treated with the combination of both drugs was observed, although this was not statistically significant.

From these results it can be concluded that chemotherapy should not impact the material and the adhesive properties of M-Trap technology. An effect of chemotherapy on the capacity of tumor cells to adhere might be expected, although this effect should impact similarly on the ability of tumor cells to adhere to the peritoneal wall and generate metastasis.

Quantification of M-Trap Tumor Cell Capture in a Time and Collagen Concentration-Dependent Manner An in vitro study determined the mode-of-action of M-Trap by evaluating the additive contribution of each element of the M-Trap device (namely, the polyurethane scaffold and the Type I collagen coating) to the tumor cell capture efficacy of the device in an in-vitro system. Tumor cell capture efficacy was assessed in an orbital adhesion assay which mimics peritoneal dissemination in ovarian cancer. M-Trap devices were immobilized in cell culture dishes. SKOV3 cells labeled with the fluorescent marker calcein were added to the plate and placed on an orbital shaker at 90 rpm for durations of 24, 48 and 72 hours at 37° C. in 5% CO2. After incubation, SKOV3 cells captured by M-Trap devices were quantified in a luminometer.

The experimental groups used were as follows:
Empty Group: Bare M-Trap scaffolds (polycarbonate polyurethane scaffold, no collagen coating).
M-Trap Low-Dose Group: M-Trap devices specially manufactured with a minimal collagen coating.
M-Trap High-Dose Group: M-Trap devices with the targeted collagen coating level designed for clinical use.

As shown in FIG. 11, the principal capture action was provided by the bare scaffold with an ancillary improved adhesive efficacy as the concentration of collagen was increased. Additionally, the linear increase in the capture efficacy as a function of incubation time further confirmed the non-pharmacological mode of action of the device.

In-Vitro Evaluation of M-Trap Tumor Cell Capture Capacity

The tumor cell saturation capacity of M-Trap in an orbital adhesion assay was evaluated. Increasing numbers of ovarian cancer cells (SKOV3) labeled with calcein were added to the plates and allowed to be captured by the device for 24 hours before quantification in a luminometer. The capacity of the device to capture six different quantities of ovarian cancer cells (1 million, 5 million, 10 million, 15 million, 20 million and 25 million) was quantified. Study results are summarized in FIG. 13. This study demonstrated that the tumor cell saturation capacity of a single M-Trap device (preclinical size) is approximately 10 million cells. Scaling the preclinical device size to the clinical size of the device, the expected saturation capacity of M-Trap in patients would be up to $1,000 \times 10^6$ metastatic cells. Since two M-Trap devices will be implanted in patients in locations where tumor cells typically disseminate, the saturation capacity of M-Trap in clinical use is up to $2,000 \times 10^6$ metastatic cells.

Mouse Model of Ovarian Cancer Peritoneal Dissemination

The non-pharmacological mode-of-action of M-Trap was demonstrated by the evaluation of the additive contribution of each element of the M-Trap device (namely, the polyurethane scaffold and the Type I collagen coating) to the tumor cell capture efficacy of the device in an in-vivo model. Tumor cell capture efficacy was assessed in a murine model of ovarian cancer peritoneal dissemination (SCID mouse) at the one-week timepoint. In this model, $1 \times 10^6$ SKOV3 ovarian cancer cells stably expressing the luciferase reporter gene were intraperitoneally injected. One week after injection, mice were sacrificed and the pattern of metastasis was analyzed by bioluminescence to determine the pattern of natural metastasis in this model system. Testing demonstrated that the pancreas and gonadal fat pad are the natural sites for SKOV3 cells implantation (FIG. 14A). Alternatively, to assess the impact of M-Trap, the device was surgically implanted at the inner wall of the peritoneum opposite to the natural sites of metastasis, one week before SKOV3 cell injection (FIG. 14B).

A total of 32 mice were used to evaluate the mode-of-action and efficacy of M-Trap in this model. A description of the experimental groups is as follows:

Control Group (n=8): One million luciferase-expressing SKOV3 cells are injected intraperitoneally. One week after tumor cell injection, the mice are sacrificed and the normal pattern of tumor cell dissemination was evaluated by bioluminescence.

Empty Group (n=8): Bare M-Trap scaffolds (polycarbonate polyurethane scaffold, no collagen coating) were surgically implanted in the inner peritoneal wall of mice. One week later, one million luciferase-expressing SKOV3 cells were injected intraperitoneally. One week after tumor cell injection, the animals were sacrificed and the pattern of tumor cell dissemination was evaluated.

M-Trap Low-Dose Group (n=8): M-Trap devices specially manufactured with a minimal collagen coating were surgically implanted in the inner peritoneal wall of mice. One week later, one million luciferase-expressing SKOV3 cells were injected intraperitoneally. One week after tumor cell injection, the animals were sacrificed and the pattern of tumor cell dissemination was evaluated.

M-Trap High-Dose Group (n=8): M-Trap devices with the targeted collagen coating level designed for clinical use were surgically implanted in the inner peritoneal wall of mice. One week later, one million luciferase-expressing SKOV3 cells were injected intraperitoneally. One week after tumor cell injection, the animals were sacrificed and the pattern of tumor cell dissemination was evaluated.

As shown in FIG. 15A, results demonstrated that the pattern of dissemination of metastatic ovarian tumor cells in the presence of M-Trap was completely remodeled, with the eradication of the natural foci of metastasis and the focalization of metastasis in a unique location within the M-Trap device. Moreover, quantification of the bioluminescence signal confirmed the non-pharmacological mode of action with the bare scaffold acting as the principal capture agent, with 65% of tumoral cells captured by the Empty scaffold (FIG. 15B). In the M-Trap Low Dose group, approximately 80% of tumoral cells were captured by M-Trap, demonstrating an improved adhesive capacity. Finally, in the M-Trap High Dose group (clinical design), 100% of tumoral cells injected were captured by M-Trap, illustrating that the optimal ancillary adhesive capacity was achieved by the clinical design.

Figure 14:
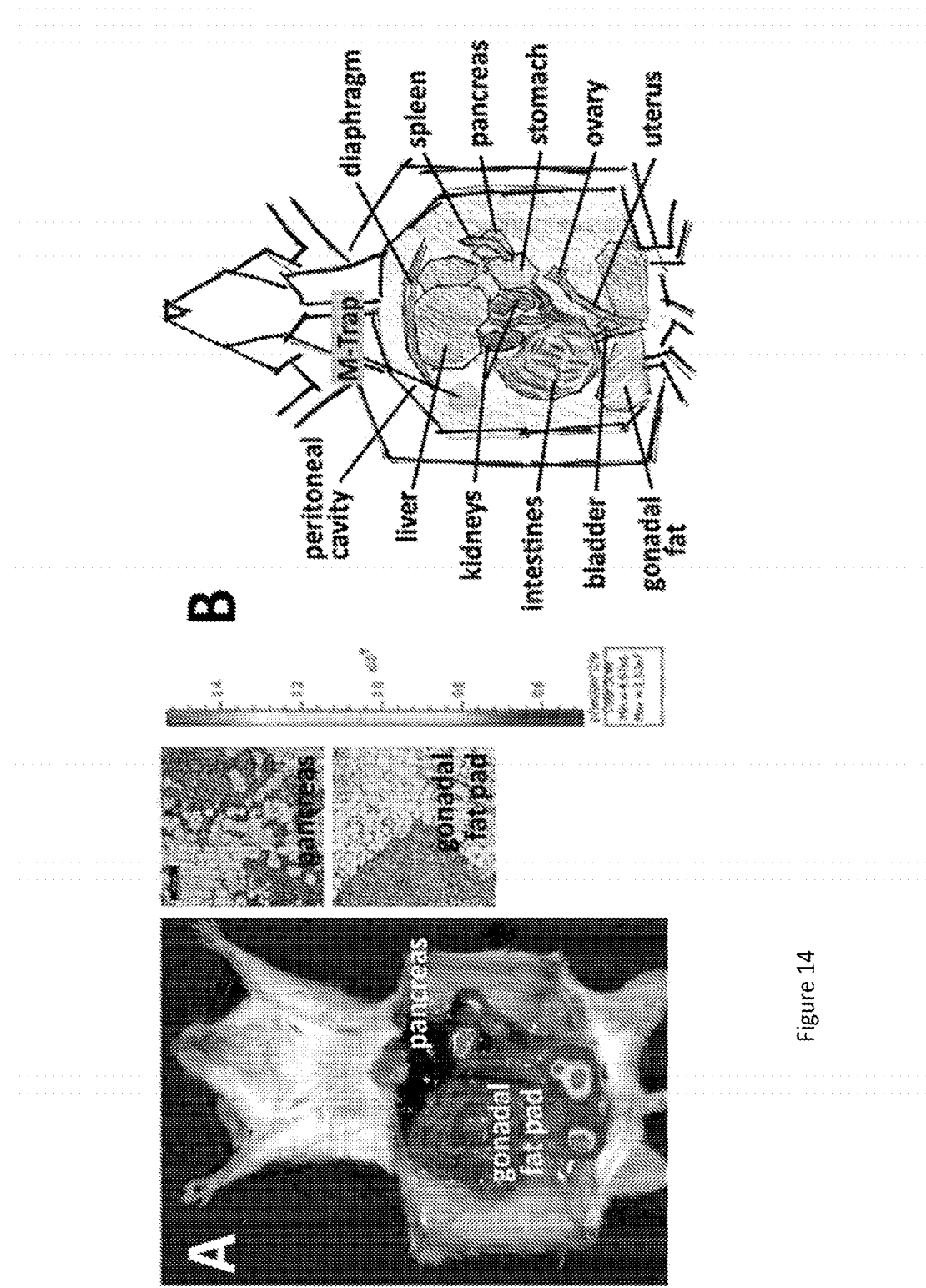
Figure 16:
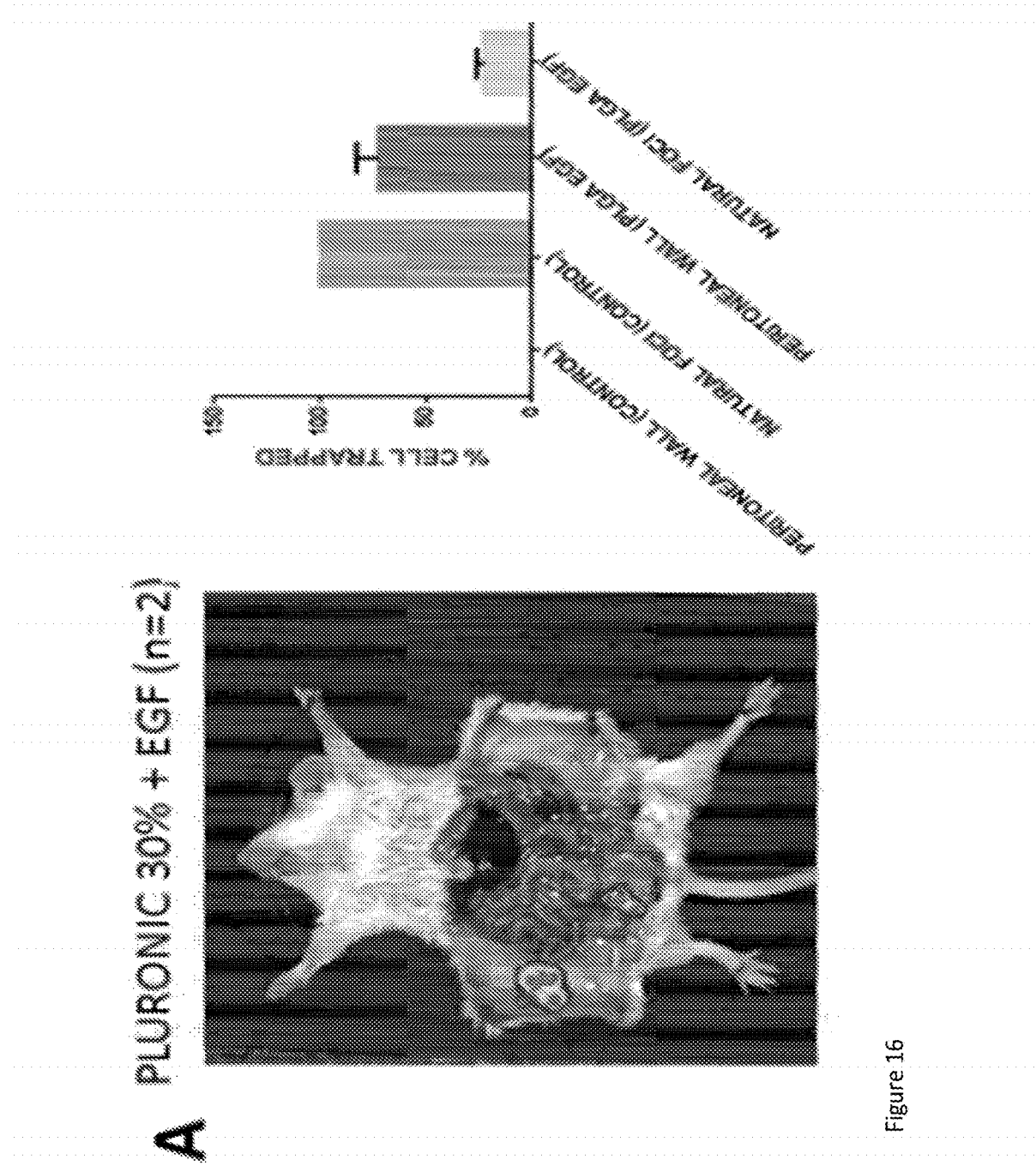
Figure 16:
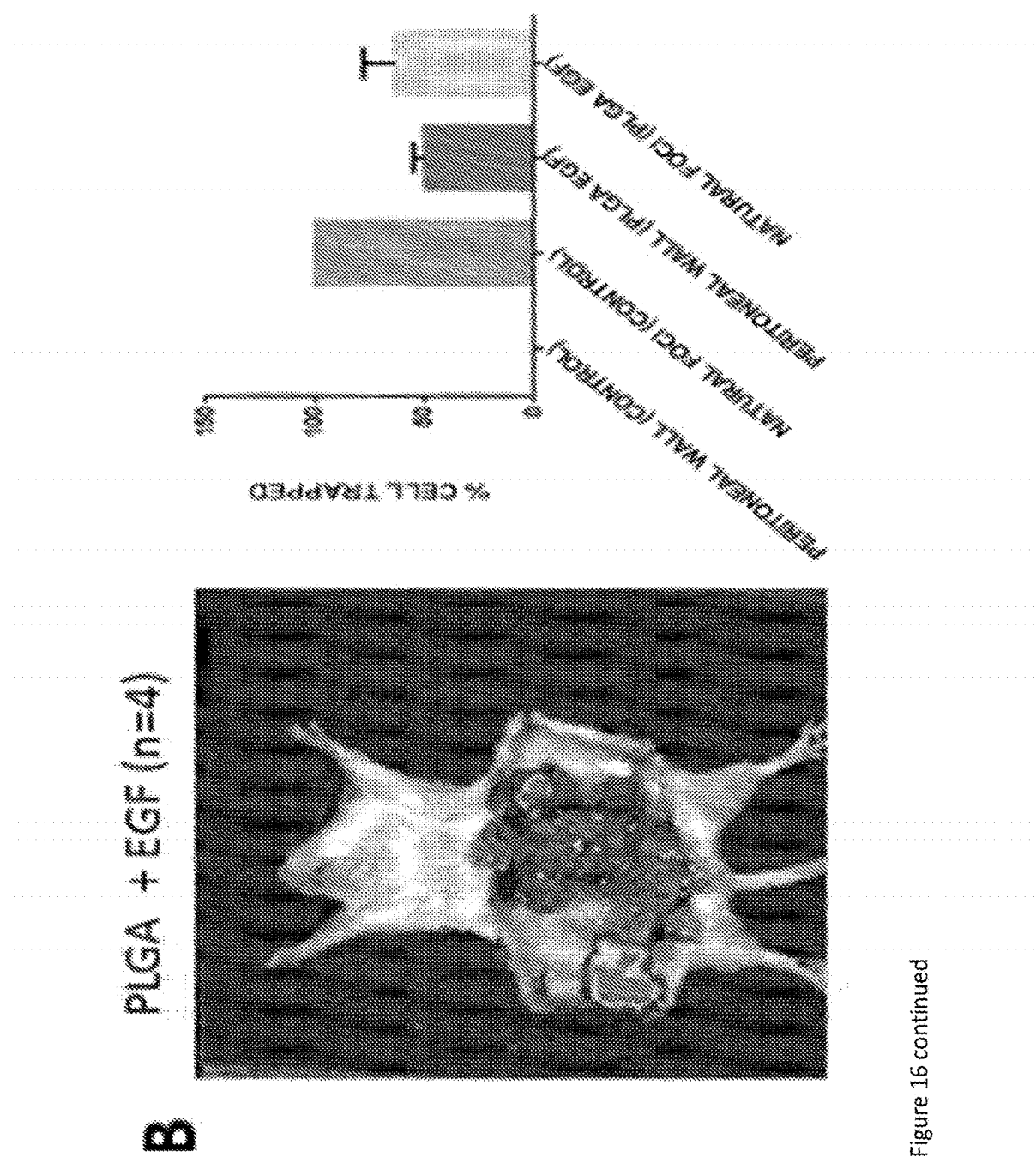

In Vivo Efficacy of Two Comparative Devices Composed of a Biodegradable Scaffold Containing the Epidermal Growth Factor (EGF) as Bioactive Protein With reference to FIG. 16, the efficacy of two comparative devices composed of a biodegradable scaffold containing the Epidermal Growth Factor (EGF) as bioactive protein were evaluated in the in vivo model described in FIG. 14. The controlled released of EGF from the scaffold generated a gradient of chemoattraction for the pharmacological capture of tumor cells in the scaffold. One of the scaffolds was fabricated by dissolving 25 mg of Xantana and 0.5 mL of EGF solution (40 mg/mL), before the addition of 750 mg Pluronic F 127, as example of hydrogel technology. The second scaffold was fabricated by dissolving 2.5 mg of poloxamin T1107+20 µg heparin+20 µg EGF in 300 µl $H_2O$, before lyophilization and resuspension in 400 ul of acetonitrile+20 mg of PLGA, further addition of 4 ml cottonseed oil+0.5% lecithin W/V, prior to 2 ml of petroleum ether for acetonitrile removal, filtration and lyophilization, as example of nanoparticle-based technology. The efficacy of both technologies was evaluated after surgical implantation in the peritoneal cavity, as described in FIG. 14. As shown in FIG. 16, representative images and quantification of captured tumor cells both by pluronic+EGF (FIG. 16A; n=2) and PLGA+EGF (FIG. 16B; n=4) devices resulted in a partial capture of ovarian tumor cells metastasizing in the peritoneal cavity. This demonstrated the competitive advantage of M-Trap technology based on polyurethane scaffold+Type I collagen coating for a complete capture of tumor cells in the peritoneal cavity and the consequent focalization of the metastatic disease. This study also demonstrated that the adhesive non-pharmacological mode of action of M-Trap technology represents an improvement over chemotactic pharmacological technologies for the capture of metastatic tumor cells in the peritoneal cavity.

Sustainability of M-Trap Tumor Cell Capture Efficacy

Also related to the differential mode of action of M-Trap, the duration of the effect and the capture ability of pharmacological competitor devices are associated with the dynamics of the release of chemoattractants. Theoretically, as the release of these factors from the scaffold decreases, the gradient of chemoattraction is reduced and the capture efficacy is gradually lost. As M-Trap behaves differentially through a non-pharmacological adhesive mode of action that is not altered, its efficacy remains intact with time. This long-term durability (sustainability) of the device to capture tumor cells has been demonstrated by evaluating the efficacy of M-Trap to capture ovarian cancer cells (SKOV3) disseminating in the peritoneal cavity in a mouse model of ovarian cancer (SCID mouse) at one, three, and six months post-implantation.

A description of the experimental groups is as follows:

M-Trap Group, One Month (n=4): M-Trap devices were surgically implanted in the inner peritoneal wall of mice. One month later, one million luciferase-expressing SKOV3 cells were injected intraperitoneally. One week after tumor cell injection, animals are sacrificed and the pattern of tumor cell dissemination is evaluated by bioluminescence.

M-Trap Group, Three Months (n=4): M-Trap devices were surgically implanted in the inner peritoneal wall of mice. Three months later, one million luciferase-expressing SKOV3 cells were injected intraperitoneally. One week after tumor cell injection, animals are sacrificed and the pattern of tumor cell dissemination is evaluated by bioluminescence.

M-Trap Group, Six Months (n=4): M-Trap devices were surgically implanted in the inner peritoneal wall of mice. Six months later, one million luciferase-expressing SKOV3 cells are injected intraperitoneally. One week after tumor cell injection, animals are sacrificed and the pattern of tumor cell dissemination is evaluated by bioluminescence.

As shown in FIG. 17, the M-Trap device captured all metastatic cells in all four (4) animals at each timepoint, confirming the efficacy of the device at one, three and six months post-implantation in an in-vivo model of metastatic ovarian peritoneal dissemination.

The ability of M-Trap to focalize the peritoneal disease and eradicate any new peritoneal metastasis linked to its particular mode of action, was demonstrated in a model of sustained release (M-Trap post-injection model in FIG. 18A-B). Moreover, the focalization of the disease resulted in a benefit in survival as demonstrated in the following preclinical study in the murine model of ovarian cancer that simulates the intended clinical use of the device. The endpoint of the study was defined as a decrease in the Performance Status of the mice, according to the Directive 2010/63/EU guideline related to the appearance, body functions, environment, behaviors, procedure-specific indicators, and free observations. Once the study endpoint was reached, the specimen was sacrificed and survival time recorded. Additionally, the pattern of tumor cell dissemination was evaluated by bioluminescence and a histological evaluation was performed.

A description of the experimental groups is schematically represented in FIG. 18A, and as follows:

Control Group (n=5): 2.5 million luciferase-expressing SKOV3 cells were injected intraperitoneally to determine survival times for the natural pattern of cancer cell dissemination and massive peritoneal carcinomatosis, in the absence of M-Trap intervention.

M-Trap Group (n=5): M-Trap devices were surgically implanted in the inner peritoneal wall of mice. One week after surgical implantation, 2.5 million luciferase-expressing SKOV3 cells were injected intraperitoneally. This group represents survival benefits attributable to M-Trap intervention and focalization of the peritoneal disease.

Re-Operated Group (n=5): M-Trap devices were surgically implanted in the inner peritoneal wall of mice. One week after surgical implantation, 2.5 million luciferase-expressing SKOV3 cells were injected intraperitoneally. After one month following tumoral cell injection, M-Trap devices were surgically removed. This group represents survival benefits attributable to M-Trap intervention and surgical removal, which is the intended clinical use of the device.

M-Trap Post-Injection Group (n=5): 2.5 million luciferase-expressing SKOV3 cells were injected intraperitoneally and allowed to disseminate to their natural sites. One month later, M-Trap devices were surgically implanted in the inner peritoneal wall of mice. This group assesses the ability of the device to capture tumor cells released from primary tumors, thereby mitigating the normal pattern of cancer cell dissemination and massive peritoneal carcinomatosis.

Representative in-vivo bioluminescence images in FIG. 18B illustrate the different patterns of peritoneal dissemination at three month follow-up in the four study groups. This interim view provides evidence of the ability of M-Trap to effectively focalize the disease (M-Trap group), and additionally illustrates that eradication of peritoneal disease is achievable by surgical removal of the device following metastatic cell capture (Re-operated group). M-Trap is also able to capture cells disseminating from primary lesions (M-Trap post-injection group), thereby mitigating the massive peritoneal carcinomatosis seen in the Control group. As shown in FIG. 18C, and Table 2, M-Trap has a significant impact on survival outcomes; Kaplan-Meyer survival curves illustrate that Control Group mice reproducibly reached the endpoint at 101 days (~3.2 months). Animals in the M-TRAP Post-Injection Group reached the study endpoint after 129 days on average (~4.3 months), demonstrating the ability of M-Trap to mitigate the peritoneal carcinomatosis seen in the Control Group without any additional intervention (i.e., reoperation). Animals in the M-Trap Group reached the study endpoint after 161.5 days on average (~5.4 months), further demonstrating the beneficial effect of focalization of the disease. Finally, mice in the Re-Operated Group had not reached the study endpoint at the five-month timepoint, demonstrating the significant survival benefits associated with the intended M-Trap clinical use. Histology in FIG. 18D confirmed the eradication of peritoneal carcinomatosis associated with the capture of metastatic tumor cells and the focalization of the disease by M-Trap technology.

week after tumor cell injection and chemotherapy, the pattern of tumor cell dissemination was evaluated.

M-Trap Group (n=5): M-Trap devices were surgically implanted in the inner peritoneal wall of mice. One week after surgical implantation, one million of luciferase-expressing SKOV3 cells were injected intraperitoneally. One week after tumor cell injection, the pattern of tumor cell dissemination was evaluated.

M-Trap IC50 Group (n=5): M-Trap devices were surgically implanted in the inner peritoneal wall of mice. One week after surgical implantation, one million luciferase-expressing SKOV3 cells were injected intraperitoneally. After 24 hours, IC50 dose of carbotaxol was administered. One week after tumor cell injection and chemotherapy, the pattern of tumor cell dissemination was evaluated.

As shown, the study results demonstrated that neither the pattern of metastasis (FIG. 19A) nor the percentage of survival tumor cells (FIG. 19B) had been modified in the presence of chemotherapy indicative of M-Trap efficacy in the presence of standard intraperitoneal chemotherapy (paclitaxel+carboplatin) used in the treatment of advanced ovarian cancer

TABLE 2

| | Days | | | | | | | | | | | | | | | | |
|---|---|---|---|---|---|---|---|---|---|---|---|---|---|---|---|---|---|
| | 0 | 87 | 94 | 101 | 104 | 112 | 115 | 126 | 129 | 133 | 136 | 145 | 157 | 166 | 210 | 220 | 265 |
| SUBJECT OF RISK | | | | | | | | | | | | | | | | | |
| Control | 5 | 5 | 4 | 3 | 2 | 1 | | | | | | | | | | | |
| Post-Injecton | 5 | | | | | | 5 | 4 | 3 | 2 | 1 | | | | | | |
| M-Trap | 4 | | | | | | | | | | | 4 | 3 | 2 | 1 | | |
| Re-operated | 2 | | | | | | | | | | | | | | | 2 | 1 |
| SURVIVAL PROPORTIONS | | | | | | | | | | | | | | | | | |
| Control | 100 | 80 | 60 | 40 | 20 | 0 | | | | | | | | | | | |
| Post-Injection | 100 | | | | | | 80 | 60 | 40 | 20 | 0 | | | | | | |
| M-Trap | 100 | | | | | | | | | | | 75 | 50 | 25 | 0 | | |
| Re-operated | 100 | | | | | | | | | | | | | | | 50 | 50 |

M-Trap Tumor Cell Capture Efficacy in the Presence of Chemotherapy

The efficacy of M-Trap to capture ovarian cancer cells (SKOV3) disseminating in the peritoneal cavity in a mouse model of ovarian cancer (SCID mouse), due to its differential mode of action resulting in the focalization of the peritoneal disease, was also demonstrated in the presence of IC50 dosage of standard chemotherapy administered intraperitoneally (carbotaxol, combination of paclitaxel+carboplatin). Because the device will be implanted in patients while they are undergoing intraperitoneal (IP) chemotherapy, this study was critical to verify device efficacy in the presence of standard IP chemotherapy regimens.

A total of 16 mice were used for this study. A description of the experimental groups is as follows:

Control Group (n=3): One million luciferase-expressing SKOV3 cells were injected intraperitoneally to evaluate the normal pattern of cancer cell dissemination. One week after tumor cell injection, the pattern of tumor cell dissemination was evaluated by bioluminescence using an in-vivo imaging system.

Control IC50 Group (n=3): One million luciferase-expressing SKOV3 cells were injected intraperitoneally. After 24 hours, IC50 dose of carbotaxol was administered. One In-Vivo Efficacy of M-Trap to Capture Different Ovarian Cancer Cells The efficacy of M-Trap to capture three additional ovarian cancer cell types was evaluated in the murine model of ovarian cancer peritoneal dissemination at one week post-implantation, in addition to the SKOV3 adenocarcinoma cell line: TOV112 (serous origin); OV90 (endometroid origin); and primary cancer cells isolated from ascitic fluid of ovarian cancer patients.

A description of the experimental groups is as follows:

TOV112 Control Group (n=3): One million luciferase-expressing TOV112 cells were injected intraperitoneally. One week after tumor cell injection, the mice were sacrificed and the normal pattern of TOV112 cell dissemination was evaluated by bioluminescence.

TOV112 M-Trap Group (n=3): M-Trap devices were surgically implanted in the inner peritoneal wall of mice. One week later, one million luciferase-expressing TOV112 cells were injected intraperitoneally. One week after tumor cell injection, the mice were sacrificed and the pattern of TOV112 cell dissemination was evaluated by bioluminescence.

OV90 Control Group (n=3): One million luciferase-expressing OV90 cells were injected intraperitoneally. One week after tumor cell injection, the mice were sacrificed and the normal pattern of OV90 cell dissemination was evaluated by bioluminescence.

OV90 M-Trap Group (n=3): M-Trap devices were surgically implanted in the inner peritoneal wall of mice. One week later, one million luciferase-expressing OV90 cells were injected intraperitoneally. One week after tumor cell injection, the mice were sacrificed and the pattern of OV90 cell dissemination was evaluated by bioluminescence.

Primary Cells Control Group (n=3): One million primary culture cells isolated from an ascitic fluid of ovarian cancer patients labeled with fluorescence marker Did were injected intraperitoneally. One week after tumor cell injection, the mice were sacrificed and the normal pattern of tumor cell dissemination was evaluated by fluorescence.

Primary Cells M-Trap Group (n=3): M-Trap devices were surgically implanted in the inner peritoneal wall of mice. One week later, one million primary culture cells isolated from an ascitic fluid of ovarian cancer patients labeled with fluorescence marker Did are injected intraperitoneally. One week after tumor cell injection, the mice are sacrificed and the pattern of tumor cell dissemination is evaluated by fluorescence.

Representative images shown in FIG. 20 demonstrated the universality of M-Trap technology to capture different clinically relevant ovarian cancer cells. The M-Trap device (right panels) completely remodeled the pattern of peritoneal dissemination shown in the control groups for TOV112, OV90 and primary ovarian cancer cells (left panels). Quantification of the bioluminescence/fluorescence signal from each group confirms the ability of M-Trap to capture all metastatic ovarian cells disseminating in the peritoneal cavity.

M-Trap Tumor Proliferation Risk

The risk of tumor growth and proliferation due to use of the M-Trap device was evaluated in a murine subcutaneous tumor model. This study was a comparative in-vivo assay in which subcutaneous SKOV3 cell tumors were generated in mice under three different conditions, with quantification of the bioluminescence signal at 2 weeks and 4 weeks to assess tumor growth and proliferation. The three different tumor conditions generated in each animal are depicted in FIG. 21A and described as follows:

Negative Control Tumor (PBS): Injection of 2.5 million SKOV3 cells resuspended in 50 microliters of phosphate buffer saline (PBS) into the right lower dorsal area of each specimen. The PBS arm represents the natural basal environment and native tumorigenic potential.

Positive Control Tumor (Matrigel): Injection of 2.5 million SKOV3 cells resuspended in 50 microliters of Matrigel into the upper dorsal area (neck) of each specimen. Matrigel is a standard protein mixture resembling the complex extracellular environment found in many tissues. The Matrigel arm represents the most favorable condition for the promotion of tumor growth.

Test Device Tumor (M-Trap): Seeding of 2.5 million SKOV3 cells within a M-Trap device and subsequent implantation of the seeded M-Trap device into the left lower dorsal area of each specimen.

As shown in FIG. 21B, M-Trap does not contribute to tumor growth upon cell capture in a murine subcutaneous tumor model. After 2 and 4 weeks, quantification of tumor growth showed similar proliferation to that of the negative control (PBS group), and significantly lower than that of the positive control (Matrigel group).

Figure 22:
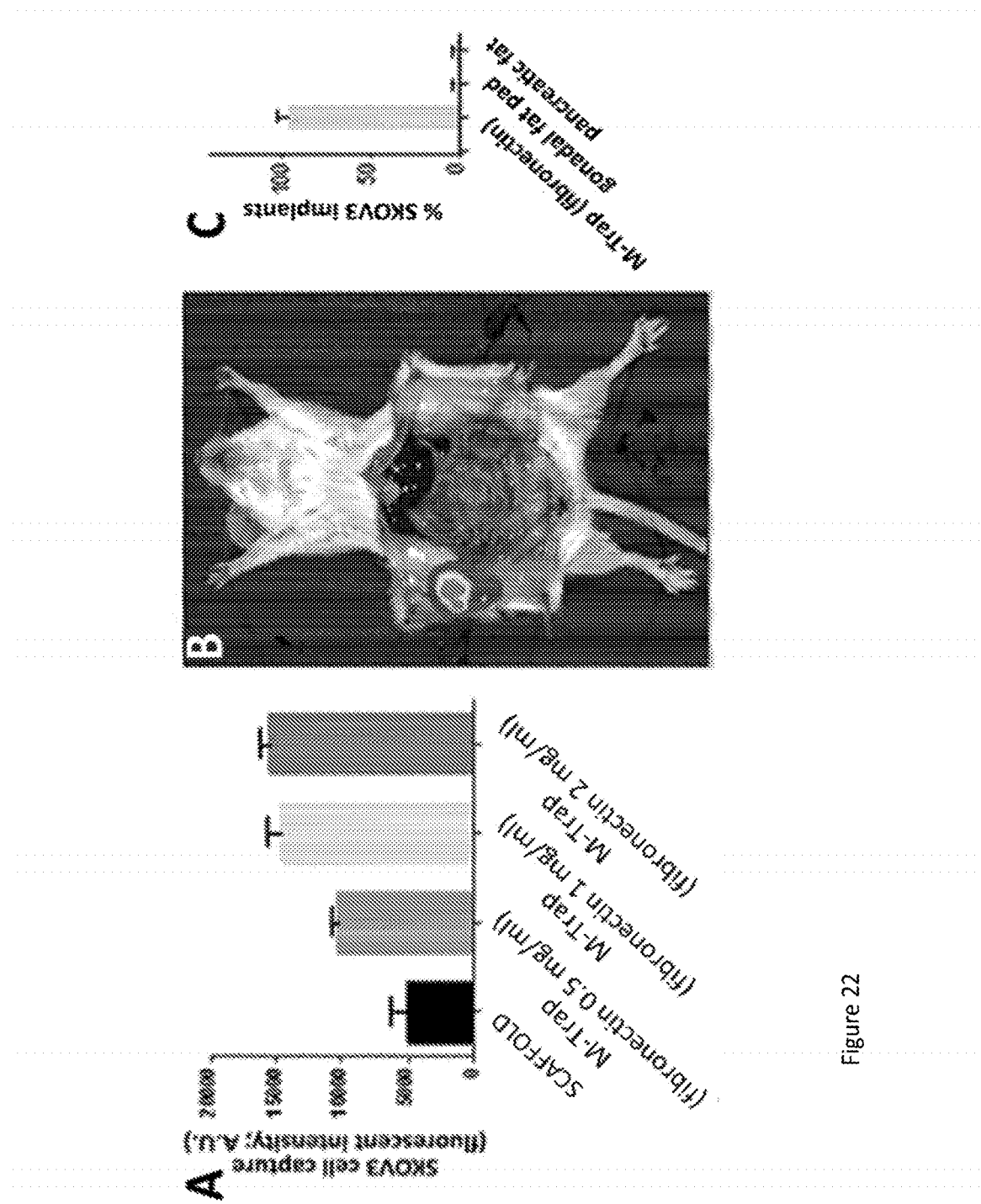

M-Trap technology efficiently captures metastatic tumor cells in an in vivo model of ovarian cancer dissemination To translate these evidences into a in vivo mice model mimicking ovarian cancer dissemination and peritoneal metastasis implantation, $1 \times 10^6$ SKOV3 cells stably expressing the luciferase reporter gene (Steinkamp at al., 2013 Front Oncol 3, 97) were intraperitoneally injected. One week later, the pattern of major natural peritoneal dissemination evaluated by bioluminescence showed the pancreas and gonadal fat pad as preferential sites of SKOV3 cells implantation (FIG. 22, panel A). To evaluate whether M-Trap might be competing with the natural foci of peritoneal metastasis and capturing cells disseminating within the peritoneal cavity, the pattern of natural peritoneal implants was compared to that generated upon implantation of the Biomerix 3D scaffold (FIG. 22, panel B) or the Biomerix 3D scaffold coated with collagen as capture agent (M-Trap; FIG. 22 panel C). For this, the device (scaffold alone or M-trap) was inserted at the inner wall of the peritoneum opposite to the pancreas and the gonadal fat pad as natural sites of meastasis. One week later, SKOV3 cells were intraperitoneally injected and the localization of metastasis was assessed seven days after injection. Remarkably, the pattern of dissemination of metastatic ovarian tumor cells in the presence of M-Trap device composed by the Biomerix scaffold decorated with 250 µg collagen was completely remodeled, with the eradication of the regular places of metastasis and the focalization of metastasis in a unique focus within the scaffold with collagen (FIG. 22, panel C). The quantification of bioluminescence signal in a series of three mice per group for natural pattern of SKOV3 cells peritoneal implants (Control), and those generated by the Biomerix scaffold without collagen (Scaffold), and M-Trap device with collagen (M-Trap), confirmed the capacity of M-Trap to capture tumor cells disseminating within the peritoneal cavity and to completely remodel the pattern of metastasis in a mice model of ovarian cancer dissemination ($p \leq 0.0001$; FIG. 22 panel D).

Similar results were obtained both in vitro and in vivo with M-Trap device composed of the Biomerix scaffold coated with the extracellular matrix protein involved in cell adhesion Fibronectin. Increasing concentrations of fibronectin decorating the scaffold were able to capture SKOV3 cells in the in vitro dynamic orbital assay mimicking transcoelomic peritoneal flow, in a dose dependent manner (FIG. 22, panel A). Similarly to the collagen adhesive properties of the M-Trap device, fibronectin coating of a Biomerix scaffold resulted in a complete remodeled pattern of peritoneal implants in the in vivo model of ovarian dissemination, with almost all metastatic tumor cells being captured within the M-Trap device (bioluminescent image of SKOV3 cells implant at M-Trap device; FIG. 22 panel B), quantified in panel FIG. 22C.

We claim:

1. A method of manufacturing an agent for modulating metastatic tumor cell dissemination, the method comprising the steps of:
   preparing a suspended solution of a cryogenically ground ECM protein;
   coating a polycarbonate polyurethane matrix by saturation within the solution of the cryogenically-ground ECM protein; and
   drying the ECM protein within the polycarbonate polyurethane matrix to form the agent for modulating metastatic tumor cell dissemination.

2. The method according to claim 1, wherein the ECM protein is ground to an average particle sire of between about 10 and 20 microns.

3. The method according to claim 1, wherein the solution of ECM protein is a solution of ECM protein and deionised water, and wherein the amount of ECM protein in solution is between about 30 and about 80 mg ECM protein/g water.

4. The method according to claim 1, wherein drying is via a lyophilisation process.

5. The method according to claim 1, further comprising crosslinking the ECM protein.

6. The method according to claim 1, wherein the ECM protein is collagen.

\* \* \* \* \*